US010722338B2

(12) United States Patent
McArthur et al.

(10) Patent No.: US 10,722,338 B2
(45) Date of Patent: Jul. 28, 2020

(54) VASCULAR FILTER DELIVERY SYSTEMS AND METHODS

(71) Applicant: Merit Medical Systems, Inc., South Jordan, UT (US)

(72) Inventors: Gregory R. McArthur, Sandy, UT (US); Wayne L. Mower, Bountiful, UT (US); Kendall Thacker, Centerville, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 27 days.

(21) Appl. No.: 14/454,297

(22) Filed: Aug. 7, 2014

(65) Prior Publication Data

US 2015/0045828 A1 Feb. 12, 2015

Related U.S. Application Data

(60) Provisional application No. 61/863,993, filed on Aug. 9, 2013.

(51) Int. Cl.
*A61F 2/01* (2006.01)
(52) U.S. Cl.
CPC ............ *A61F 2/01* (2013.01); *A61F 2002/011* (2013.01); *A61F 2002/018* (2013.01); *A61F 2230/005* (2013.01); *A61F 2230/0076* (2013.01)
(58) Field of Classification Search
CPC .... A61F 2/01; A61F 2/95; A61F 2/962; A61F 2/966; A61F 2/2427; A61F 2/2436; A61F 2002/011; A61F 2002/013; A61F 2002/015; A61F 2002/016; A61F 2002/018;

(Continued)

(56) References Cited

U.S. PATENT DOCUMENTS

| 4,132,650 A | 1/1979 | Krisch et al. |
| 4,359,960 A * | 11/1982 | Burchett ................. B63B 21/26 |
| | | 114/294 |
| 4,494,531 A | 1/1985 | Gianturco |

(Continued)

FOREIGN PATENT DOCUMENTS

| EP | 0350043 | 8/1992 |
| EP | 1987800 | 4/2008 |

(Continued)

OTHER PUBLICATIONS

Definition of Coupling: Merriam-Webster:http://www.merriam-webster.com/dictionary/coupling.*

(Continued)

*Primary Examiner* — Ryan J. Severson
*Assistant Examiner* — Socrates L Boutsikaris
(74) *Attorney, Agent, or Firm* — Stoel Rives LLP

(57) ABSTRACT

A filter configured to be disposed within the vasculature to capture or trap material within a body lumen is disclosed. The filter may be configured to be removable and may be configured to slice through ingrown or encapsulated tissue during removal. A filter deployment device or system which may be configured to deliver a filter or filters to a position within a body lumen, such as within the vasculature, is also disclosed. The filter deployment device may be configured to limit inadvertent decoupling of a filter. Also, the filter deployment device may be configured to retrieve a deployed filter.

19 Claims, 18 Drawing Sheets

(58) Field of Classification Search
CPC ...... A61F 2002/9517; A61F 2002/9528; A61F 2002/9534; A61F 2002/9665
USPC .............................. 606/198, 200; 623/1.11
See application file for complete search history.

(56) References Cited

U.S. PATENT DOCUMENTS

| | | | |
|---|---|---|---|
| 4,619,246 A | 10/1986 | Molgaard-Nielsen | |
| 4,781,177 A | 11/1988 | Lebigot | |
| 4,832,005 A | 5/1989 | Palestrant | |
| 4,900,312 A | 2/1990 | Nadeau | |
| 5,133,733 A | 7/1992 | Rasmussen et al. | |
| 5,234,458 A | 8/1993 | Metais | |
| 5,242,462 A | 9/1993 | El-Nounou et al. | |
| 5,312,479 A | 5/1994 | Weinstein et al. | |
| 5,324,304 A | 6/1994 | Rasmussen | |
| 5,370,657 A | 12/1994 | Irie | |
| 5,375,612 A | 12/1994 | Cottenceau et al. | |
| 5,437,655 A | 8/1995 | Bartholomew | |
| 5,484,474 A | 1/1996 | Weinstein et al. | |
| 5,601,568 A | 2/1997 | Chevillon et al. | |
| 5,626,605 A | 5/1997 | Irie | |
| 5,634,942 A | 6/1997 | Chevillon et al. | |
| 5,669,933 A | 9/1997 | Simon | |
| 5,709,704 A | 1/1998 | Nott et al. | |
| 5,795,322 A | 8/1998 | Boudewijn | |
| 5,810,874 A | 9/1998 | Lefebvre | |
| 5,836,968 A | 11/1998 | Simon et al. | |
| 5,836,969 A | 11/1998 | Kim | |
| 5,853,420 A | 12/1998 | Chevillon et al. | |
| 5,879,381 A | 3/1999 | Moriuchi | |
| 5,954,741 A | 9/1999 | Fox | |
| 5,976,172 A | 11/1999 | Homsma et al. | |
| 5,984,947 A | 11/1999 | Smith | |
| 6,007,557 A * | 12/1999 | Ambrisco | A61F 2/01 606/159 |
| 6,007,558 A | 12/1999 | Ravenscroft et al. | |
| 6,013,093 A | 1/2000 | Nott et al. | |
| 6,059,825 A | 5/2000 | Hobbs | |
| 6,099,549 A | 8/2000 | Bosma et al. | |
| 6,117,165 A | 9/2000 | Becker | |
| 6,156,055 A | 12/2000 | Ravenscroft | |
| 6,193,739 B1 | 2/2001 | Chevillon et al. | |
| 6,214,025 B1 | 4/2001 | Thistle et al. | |
| 6,241,746 B1 | 6/2001 | Bosma et al. | |
| 6,258,026 B1 | 7/2001 | Ravenscroft et al. | |
| 6,267,777 B1 | 7/2001 | Bosma et al. | |
| 6,273,900 B1 | 8/2001 | Nott et al. | |
| 6,273,901 B1 | 8/2001 | Whitcher et al. | |
| 6,306,141 B1 | 10/2001 | Jervis | |
| 6,328,719 B1 | 12/2001 | Holtermann et al. | |
| 6,347,711 B1 | 2/2002 | Goebel et al. | |
| 6,391,045 B1 | 5/2002 | Kim | |
| 6,428,559 B1 | 8/2002 | Johnson | |
| 6,436,121 B1 | 8/2002 | Blom | |
| 6,443,972 B1 | 9/2002 | Bosma | |
| 6,461,370 B1 | 10/2002 | Gray et al. | |
| 6,468,290 B1 | 10/2002 | Weldon et al. | |
| 6,485,501 B1 | 11/2002 | Green | |
| 6,506,205 B2 | 1/2003 | Goldberg et al. | |
| 6,511,496 B1 | 1/2003 | Huter et al. | |
| 6,527,962 B1 | 3/2003 | Nadal | |
| 6,540,722 B1 | 4/2003 | Boyle et al. | |
| 6,540,768 B1 | 4/2003 | Diaz et al. | |
| 6,589,266 B2 | 7/2003 | Whitcher et al. | |
| 6,596,011 B2 | 7/2003 | Johnson et al. | |
| 6,620,183 B2 | 9/2003 | DiMatteo | |
| 6,623,506 B2 | 9/2003 | McGuckin, Jr. et al. | |
| 6,656,203 B2 | 12/2003 | Roth et al. | |
| 6,660,021 B1 | 12/2003 | Palmer et al. | |
| 6,726,701 B2 | 4/2004 | Gilson | |
| 6,783,538 B2 | 8/2004 | McGuckin, Jr. et al. | |
| 6,793,665 B2 | 9/2004 | McGuckin, Jr. et al. | |
| 6,932,831 B2 | 8/2005 | Forber | |
| 6,939,361 B1 | 9/2005 | Kleshinski | |
| 6,958,074 B2 | 10/2005 | Russell | |
| 6,989,021 B2 | 1/2006 | Bosma | |
| 6,991,641 B2 | 1/2006 | Diaz et al. | |
| 7,147,649 B2 | 12/2006 | Thomas | |
| 7,179,275 B2 | 2/2007 | McGuckin | |
| 7,261,731 B2 | 8/2007 | Patel | |
| 7,279,000 B2 | 10/2007 | Cartier et al. | |
| 7,314,477 B1 | 1/2008 | Ravenscroft et al. | |
| 7,323,002 B2 | 1/2008 | Johnson et al. | |
| 7,329,227 B2 | 2/2008 | Schramm | |
| 7,329,269 B2 | 2/2008 | Shapiro et al. | |
| 7,329,277 B2 | 2/2008 | Schramm | |
| 7,338,512 B2 | 3/2008 | McGuckin, Jr. et al. | |
| 7,344,549 B2 | 3/2008 | Boyle et al. | |
| 7,399,308 B2 | 7/2008 | Borillo et al. | |
| 7,582,100 B2 | 1/2009 | Johnson | |
| 7,534,251 B2 | 5/2009 | WasDyke | |
| 7,544,202 B2 | 6/2009 | Cartier et al. | |
| 7,625,390 B2 | 12/2009 | Hendriksen et al. | |
| 7,699,865 B2 | 4/2010 | Johnson et al. | |
| 7,699,867 B2 | 4/2010 | Hendriksen et al. | |
| 7,704,266 B2 | 4/2010 | Thinnes, Jr. et al. | |
| 7,704,267 B2 | 4/2010 | Tessmer | |
| 7,736,383 B2 | 6/2010 | Bressler et al. | |
| 7,749,246 B2 | 7/2010 | McGuckin et al. | |
| 7,763,045 B2 | 7/2010 | Osborne | |
| 7,771,452 B2 | 8/2010 | Pal et al. | |
| 7,780,694 B2 | 8/2010 | Palmer et al. | |
| 7,794,473 B2 | 9/2010 | Tessmer et al. | |
| 7,803,171 B1 | 9/2010 | Uflacker | |
| 7,862,577 B2 | 1/2011 | Gray et al. | |
| 7,887,561 B2 | 2/2011 | McGuckin, Jr. et al. | |
| 7,909,847 B2 | 3/2011 | McGuckin, Jr. et al. | |
| 7,931,664 B2 | 4/2011 | Gray et al. | |
| 7,959,647 B2 | 6/2011 | Palmer | |
| 7,967,838 B2 | 6/2011 | Chanduszko et al. | |
| 7,972,353 B2 | 7/2011 | Hendriksen et al. | |
| 7,976,562 B2 | 7/2011 | Bressler et al. | |
| 7,996,993 B2 | 8/2011 | Gray et al. | |
| 8,025,675 B2 | 9/2011 | Shirley et al. | |
| 8,029,529 B1 | 10/2011 | Chankduszko | |
| 8,043,322 B2 | 10/2011 | Hendriksen et al. | |
| 8,057,506 B2 | 11/2011 | Gilson et al. | |
| 8,057,507 B2 | 11/2011 | Horan et al. | |
| 8,062,326 B2 | 11/2011 | McGuckin, Jr. et al. | |
| 8,062,327 B2 | 11/2011 | Chanduszko et al. | |
| 8,062,328 B2 | 11/2011 | Hallisey | |
| 8,092,484 B2 | 1/2012 | Kashkarov et al. | |
| 8,092,485 B2 | 1/2012 | Lapid | |
| 8,100,936 B2 | 1/2012 | McGuckin, Jr. et al. | |
| 8,105,349 B2 | 1/2012 | Hendriksen et al. | |
| 8,118,828 B2 | 2/2012 | Cartier et al. | |
| 8,133,251 B2 | 3/2012 | Ravenscroft et al. | |
| 8,133,252 B2 | 3/2012 | Davis et al. | |
| 8,162,972 B2 | 4/2012 | McGuckin, Jr. et al. | |
| 8,167,901 B2 | 5/2012 | Hendriksen et al. | |
| 8,211,140 B2 | 7/2012 | McGunkin, Jr. et al. | |
| 8,246,648 B2 | 8/2012 | Tekulve | |
| 8,246,650 B2 | 8/2012 | Osborne | |
| 8,246,651 B2 | 8/2012 | Hendriksen et al. | |
| 8,252,019 B2 | 8/2012 | Fleming, III | |
| 8,252,817 B2 | 8/2012 | Paul, Jr. et al. | |
| 8,267,954 B2 | 9/2012 | Decant, Jr. et al. | |
| 8,282,668 B2 | 10/2012 | McGuckin, Jr. et al. | |
| 8,298,211 B2 * | 10/2012 | Zimmer | A61B 90/39 604/506 |
| 8,317,818 B2 | 11/2012 | Kashkarov et al. | |
| 8,333,785 B2 | 12/2012 | Chanduszko et al. | |
| 8,353,926 B2 | 1/2013 | Silver | |
| 8,366,736 B2 | 2/2013 | Thinnes, Jr. et al. | |
| 8,383,926 B2 | 2/2013 | Plissonnier et al. | |
| 8,430,093 B1 | 4/2013 | Chanduszko et al. | |
| 8,430,903 B2 | 4/2013 | Chanduszko et al. | |
| 8,475,488 B2 | 7/2013 | Cartier et al. | |
| 8,734,480 B2 | 5/2014 | Snow | |
| 9,028,525 B2 | 5/2015 | Hallisey | |
| 2001/0000799 A1 | 5/2001 | Wessman et al. | |
| 2001/0039432 A1 | 11/2001 | Whitcher et al. | |

(56) References Cited

U.S. PATENT DOCUMENTS

| | | | |
|---|---|---|---|
| 2002/0052627 A1* | 5/2002 | Boylan | A61F 2/013 606/200 |
| 2002/0058911 A1 | 5/2002 | Gilson et al. | |
| 2002/0062134 A1 | 5/2002 | Barbut et al. | |
| 2002/0111647 A1 | 8/2002 | Khairkhahan et al. | |
| 2003/0109897 A1 | 6/2003 | Walak et al. | |
| 2003/0181942 A1* | 9/2003 | Sutton | A61B 17/0057 606/200 |
| 2004/0082966 A1 | 4/2004 | Wasdyke | |
| 2004/0087999 A1 | 5/2004 | Bosma et al. | |
| 2004/0116959 A1 | 6/2004 | McGuckin | |
| 2004/0220610 A1 | 11/2004 | Kriedler et al. | |
| 2005/0004596 A1 | 1/2005 | McGuckin, Jr. et al. | |
| 2005/0015111 A1 | 1/2005 | McGuckin et al. | |
| 2005/0080447 A1 | 4/2005 | McCuckin, Jr. et al. | |
| 2005/0222604 A1 | 10/2005 | Shaeffer | |
| 2005/0267515 A1 | 12/2005 | Oliva et al. | |
| 2005/0288704 A1 | 12/2005 | Cartier et al. | |
| 2005/0288705 A1 | 12/2005 | Gilson | |
| 2006/0009799 A1 | 1/2006 | Kleshinski et al. | |
| 2006/0015136 A1* | 1/2006 | Besselink | A61F 2/013 606/200 |
| 2006/0041271 A1 | 2/2006 | Bosma et al. | |
| 2006/0079928 A1 | 4/2006 | Cartier | |
| 2006/0079930 A1 | 4/2006 | McGuckin et al. | |
| 2006/0100659 A1 | 5/2006 | Dinh et al. | |
| 2006/0106417 A1 | 5/2006 | Tessmer | |
| 2006/0155320 A1* | 7/2006 | Bressler | A61F 2/01 606/200 |
| 2006/0206138 A1 | 9/2006 | Eidenschink | |
| 2006/0241411 A1* | 10/2006 | Field | A61B 90/39 600/431 |
| 2007/0005095 A1 | 1/2007 | Osborne | |
| 2007/0141107 A1 | 6/2007 | Kutryk | |
| 2007/0162048 A1 | 7/2007 | Quinn et al. | |
| 2007/0162071 A1* | 7/2007 | Burkett | A61F 2/01 606/200 |
| 2007/0167974 A1 | 7/2007 | Cully et al. | |
| 2007/0173885 A1 | 7/2007 | Cartier | |
| 2007/0191932 A1 | 8/2007 | Kutryk | |
| 2007/0198050 A1 | 8/2007 | Ravenscroft | |
| 2008/0027481 A1 | 1/2008 | Gilson | |
| 2008/0033479 A1 | 2/2008 | Silver | |
| 2008/0097518 A1 | 4/2008 | Thinnes | |
| 2008/0234722 A1 | 9/2008 | Bonnette et al. | |
| 2008/0275487 A1 | 11/2008 | Fleming | |
| 2008/0275492 A1 | 11/2008 | Farmiga | |
| 2009/0043332 A1 | 2/2009 | Sullivan et al. | |
| 2009/0069840 A1 | 3/2009 | Hallisey | |
| 2009/0074728 A1* | 3/2009 | Gronthos | C07K 16/40 424/93.7 |
| 2009/0198270 A1 | 8/2009 | McGuckin, Jr. et al. | |
| 2009/0254117 A1 | 10/2009 | Pakter | |
| 2009/0299403 A1 | 12/2009 | Chanduszko et al. | |
| 2009/0299404 A1 | 12/2009 | Chanduszko et al. | |
| 2009/0306703 A1 | 12/2009 | Kashkarov et al. | |
| 2010/0049238 A1 | 2/2010 | Simpson | |
| 2010/0174310 A1 | 7/2010 | Tessmer | |
| 2010/0185229 A1 | 7/2010 | Horan et al. | |
| 2010/0185230 A1 | 7/2010 | Horan et al. | |
| 2010/0198252 A1 | 8/2010 | Beyer et al. | |
| 2010/0318115 A1 | 12/2010 | Chanduszko et al. | |
| 2011/0028836 A1* | 2/2011 | Ranpura | A61B 90/39 600/432 |
| 2011/0040321 A1 | 2/2011 | Cartier | |
| 2011/0106133 A1 | 5/2011 | O'Connell et al. | |
| 2011/0137335 A1 | 6/2011 | Hallisey et al. | |
| 2011/0166593 A1 | 7/2011 | Paul, Jr. | |
| 2011/0202086 A1 | 8/2011 | Bates | |
| 2011/0208233 A1 | 8/2011 | McGuckin, Jr. et al. | |
| 2012/0016471 A1* | 1/2012 | Salahieh | A61F 2/2418 623/2.11 |
| 2012/0089173 A1 | 4/2012 | Tukulve | |
| 2012/0109181 A1 | 5/2012 | Hallisey | |
| 2012/0130418 A1 | 5/2012 | Jenson et al. | |
| 2012/0184985 A1 | 7/2012 | Ravenscroft et al. | |
| 2012/0245622 A1 | 9/2012 | McGuckin, Jr. et al. | |
| 2013/0018387 A1 | 1/2013 | Diamant | |
| 2013/0035713 A1 | 2/2013 | Snow | |
| 2013/0035714 A1 | 2/2013 | Snow | |
| 2014/0214046 A1* | 7/2014 | Puckett | A61F 2/966 606/108 |
| 2016/0008003 A1* | 1/2016 | Kleshinski | A61B 17/12031 606/200 |

FOREIGN PATENT DOCUMENTS

| | | |
|---|---|---|
| JP | 61/41444 | 5/1994 |
| JP | 2008/154276 | 7/2008 |
| WO | WO2001/10342 | 2/2001 |
| WO | WO2002/071977 | 9/2002 |
| WO | WO2007/084431 | 7/2007 |
| WO | 2008042266 | 4/2008 |
| WO | 2008051294 A2 | 5/2008 |
| WO | WO2008/127328 | 10/2008 |
| WO | WO2009/032834 | 3/2009 |
| WO | WO2010/091118 | 8/2010 |
| WO | 2012088346 | 6/2012 |
| WO | 2013071054 | 5/2013 |
| WO | 2015/021296 A1 | 2/2015 |

OTHER PUBLICATIONS

Definition of decoupling: Merriam-Webster:http://www.merriam-webster.com/dictionary/decouple.*
U.S. Appl. No. 13/774,598, filed Feb. 22, 2013, Snow.
Boothroyd et al., 'Product Design for Manufacture and Assembly.' 1994, p. 64.
International Preliminary Report for Application No. PCT/US08/75102 dated Sep. 3, 2008.
International Publication and Written Opinion for Application No. PCT/US08/75102 dated Mar. 12, 2009.
Cipolla et al., 'Complications of Vena Cava Filters: A Comprehensive Clinical Review.' OPUS 12 Scientist 2008; vol. 2, No. 2: 11-24.
Extended European Search Report dated Nov. 20, 2014 for EP12821778.3.
Notice of Allowance dated Jun. 7, 2016 for U.S. Appl. No. 13/774,598.
Notice of Allowance dated Mar. 27, 2015 for U.S. Appl. No. 13/286,653.
Office Action dated Apr. 10, 2014 for U.S. Appl. No. 13/286,653.
Extended European Search Report dated Nov. 20, 2014 for EP12822068.8.
Prince et al., 'The diameter of the inferior Vena Cava and It's Implications for the Use of Vena Caval Filters.' Radiology 1983; 149:687-689.
Simon et al., 'Comparative Evaluation of Clinically Available Inferior Vena Cava Filters with an In Vitro Physiologic Simulation of the Vena Cava.' Radiology 1993; 189:769-774.
Lorch et al., 'In Vitro Studies of Temporary Vena Cava Filters.' CardioVascular and Interventional Radiology 1998; 21:146-150.
Neuerburg et al., 'New Retrievable Percutaneous Vena Cava Filter: Experimental In Vitro and In Vivo Evaluation.' CardioVascular and Interventional Radiology 1993: 16:224-229.
Reekers et al., 'Evaluation of the Retrievability of the OptEase IVC Filter in an Animal Model.' J Vasc Interv Radiol 2004; 15:261-267.
Kinney, 'Update on Inferior Vena Cava Filters.' J Vasc Interv Radiol 2003; 14:425-440.
Bruckheimer et al., 'In Vitro Evaluation of a Retrievable Low-Profile Nitinol Vena Cava Filter.' J Vasc Interv Radiol 2003; 14:469-474.
Brountzos et al., 'A New Optional Vena Cava Filter: Retrieval at 12 Weeks in an Animal Model.' J Vasc Interv Radiol 2003; 14:763-772.
Ray et al., 'Outcomes with Retrievable Inferior Vena Cava Filters: A Multicenter Study.' J Vasc Interv Radiol 2006; 17:1595-1604.
Kaufman et al., 'Guidelines for the Use of Retrievable and Convertible Vena Cava Filters: Report from the Society of Interventional Radiology Mulitdisciplinary consensus conference.' J Vasc Interv Radiol 2006; 17:449-459.

(56) References Cited

OTHER PUBLICATIONS

Kolbeck et al., 'Optional Inferior Vena Cava Filter Retrieval with Retained Thrombus: An In Vitro Model.' J Vasc Interv Radiol 2006; 17:685-691.
Lorch et al., 'Current Practice of Temporary Vena Cava Filter Insertion: A Multicenter Registry.' JVIR 2000; 11:83-88.
Rousseau et al., 'The 6-F Nitinol TrapEase Inferior Vena Cava Filter: Results of a Prospective Multicenter Trial.' J Vasc Interv Radiol 2001; 12:299-304.
Stoneham et al., 'Temporary Inferior Vena Cava Filters: In Vitro Comparison with Permanent IVC Filters.' JVIR 1995; 6:731-736.
Crochet et al., 'Evaluation of the LGM Vena Cava-Tech Infrarenal Vena Cava Filter in and Ovine Venous Thromboembolism Model.' J Vasc Interv Radiol 2001; 12:739-745.
Kaufman, 'Guidelines for the Use of Optional Retrievable Vena Cava Filters.' European Respiratory Disease 2007; 31-34.
Epstein et al., 'Experience with the Amplatz Retrievable Vena Cava Filter.' Radiology 1989; 172:105-110.
Inferior Vena Cava Filter, ISI Interventional & Surgical Innovations LLC. Product Brochure, Copyright 2008.
The Clot Stopper (online). Retrieved from the internet URL:http:/www.americanheritage.com/people/articles/web/20060715-pulmonary-embolism-blood-clot-lazar-greenfield-garman-kimmel-surgery-medical-doctor-surgeon.shtml Summer 2006, vol. 22 Issue 1.
Simon Nitinol Filter, Versatile and Dependable Performance. Bard Peripheral Vascular (online). Retrieved from the internet URL:http://www.bardpv.com_vascular/product.php?p=23 Copyright 2004.
Aegisy Vena Cava Filter. Shenzhen Lifetech Scientific Inc. (online). Retrieved from the internet URL:http://www.lifetechmed.com/english/product/product6.htm Copyright 2005.
Safe Flo Vena Cava Filter (online). Retrieved from the internet URL:www.rafaelmedical.com Accessed Feb. 18, 2009.
Aegisy Vena Cava Filter Product Description (online). Retrieved from the internet URL:http://www.lifetechclinic.com/upload/article/vena/instruction_for_use.htm Accessed Jun. 6, 2008.
Design History (online). Retrieved from the internet URL:http://www.lifetechclinic.com/upload/article/vena/vena_cava_filter.htm Accessed Jun. 6, 2008.
Crux Biomedical, Inc. Inferior Vena Cava Filter System Instructions for Use, IFU P/N 0001 Rev.B, DCO# 0027, Effective Date Feb. 2, 2007.
Smouse, 'Next Generation Filters: Are There Improvements Over the Existing Filters?', Powerpoint Presentation. University of Illinois College of Medicine at Peoria. Feb. 2009.
Kaufman, 'Vena Cava Filters as a Risk Factor for VTE'. Powerpoint Presentation at the SIR Foundation Jun. 2007 IVC Filter Research Consensus Panel.
Rectenwald, 'Are All IVC's the Same.' Powerpoint Presentation at the SIR Foundation Jun. 2007 IVC Filter Research Consensus Panel.
Rogers, 'Vena Cava Filter Outcomes.' Powerpoint Presentation at the SIR Foundation Jun. 2007 IVC Filter Research Consensus Panel.
SIR Foundation Research Consensus Panel for the Development of a Research Agenda in Inferior Vena Cava Filters, Jun. 12, 2007—Herndon, VA. Powerpoint Presentation at the SIR Foundation Jun. 2007 IVC Filter Research Consensus Panel.
TrapEase Vena Cava Filter User's Instruction. Cordis Corp. Dated Feb. 18, 2009.
Corriere et al., 'Vena Cava Filters: An Update.' Future Cardiol 2006: 2(6): 695-707.
Mohan, C. et al. 'Comparative Efficacy and Complications of Vena Caval Filters.' J Vasc Surg 1995; 21:235-246.
Linsenmaier, U. et al., 'Indications, Management, and Complications of Temporary Inferior Vena Cava Filters.' Cardiovascular Intervent, Radiol 1998; 21(6): 464-469.
Asch et al. Radiology 2002; 29:173-176.
Cunliffe et al., 'A Fatal Complication of a Vena Cava Filter Associated with Pulmonary Thromboembolism.' Am J Forensic Med Pathol 2008; 29:173-176.
Joels et al., 'Complications of Inferior Vena Cava Filters.' Am Surg 2003; 69:654-659.
Pulmonary Embolism (online). Retrieved from internet URL:http//www.mayoclinic.com/health/pulmonary-embolism/DS00429/DSECTION=complications By Mayo Clinic Staff Sep. 28, 2007.
Cordis TrapEase Permanent Vena Cava Filter with the VisEase Angiographic Vessel Dilator (on line). Retrieved from <URL:http//www.mitek.com/home.jhtml?loc=USENG&page=viewcontent&contentid=09008b9880ffdcbf&nodekey=1Prod_Info/Type/Endovascular_Disease_Management/Vena_Cava_Filters&parentid=fc0de00100001215> 2000-2008.
Decousus et al., 'A Clinical Trial of Vena Caval Filters in the Prevention of Pulmonary Embolism in Patients with Proximal Deep-Vein Thrombosis.' The New England Journal of Medicine, Feb. 12, 1998; vol. 338, No. 7.
Notice of Allowance for U.S. Appl. No. 12/203,515 dated Jul. 13, 2011.
Restriction Requirement dated Nov. 21, 2011 for U.S. Appl. No. 12/722,484.
Office Action dated Mar. 6, 2012 for U.S. Appl. No. 12/722,484.
International Search Report and Written Opinion dated Jan. 30, 2013 for PCT/US2012/047004.
International Search Report and Written Opinion dated Jan. 30, 2013 for PCT/US2012/047023.
Office Action dated Mar. 29, 2013 for U.S. Appl. No. 13/204,462.
Office Action dated Mar. 29, 2013 for U.S. Appl. No. 13/204,492.
International Search and Written Opinion dated Jun. 13, 2013 for PCT/US2013/027427.
Office Action dated Oct. 3, 2013 for U.S. Appl. No. 12/722,484.
Office Action dated Oct. 17, 2013 for U.S. Appl. No. 13/204,492.
Notice of Allowance dated Feb. 14, 2014 for U.S. Appl. No. 13/204,492.
Notice of Allowance dated Feb. 12, 2014 for U.S. Appl. No. 13/204,462.
Notice of Allowance dated Apr. 16, 2014 for U.S. Appl. No. 12/722,484.
Office Action dated Sep. 22, 2014 for U.S. Appl. No. 13/286,653.
International Search Report and Written Opinion dated Nov. 13, 2014 for PCT/US2014/050176.
International Search Report and Written Opinion dated Feb. 18, 2016 for PCT/US2014/050176.
International Search Report and Written Opinion dated Nov. 10, 2008 for PCT/US2008/75102.
Katsamouris et al., 'Inferior Vena Cava Filters: In Vitro Comparison of Clot Trapping and Flow Dynamics', Radiology 1988, 166:361-366.
Office Action dated Feb. 11, 2016 for U.S. Appl. No. 13/774,598.
European Search Report dated Dec. 19, 2016 for EP14835067.1.
Extended European Search Report dated May 4, 2015 for EP13751892.4.
International Preliminary Report dated Mar. 9, 2010 for PCT/US2008/75102.
Office Action dated Sep. 26, 2012 for U.S. Appl. No. 12/722,484.

* cited by examiner

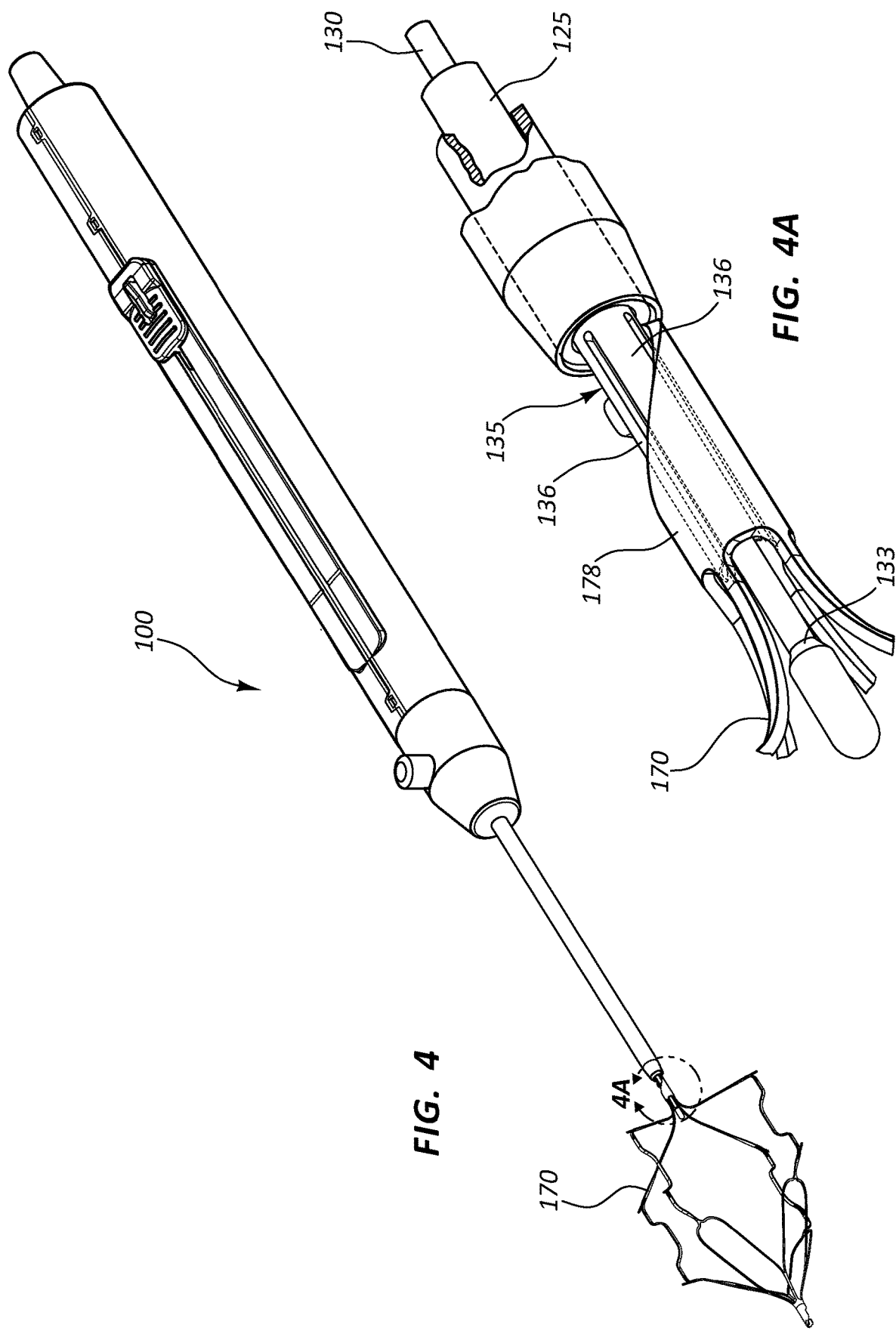

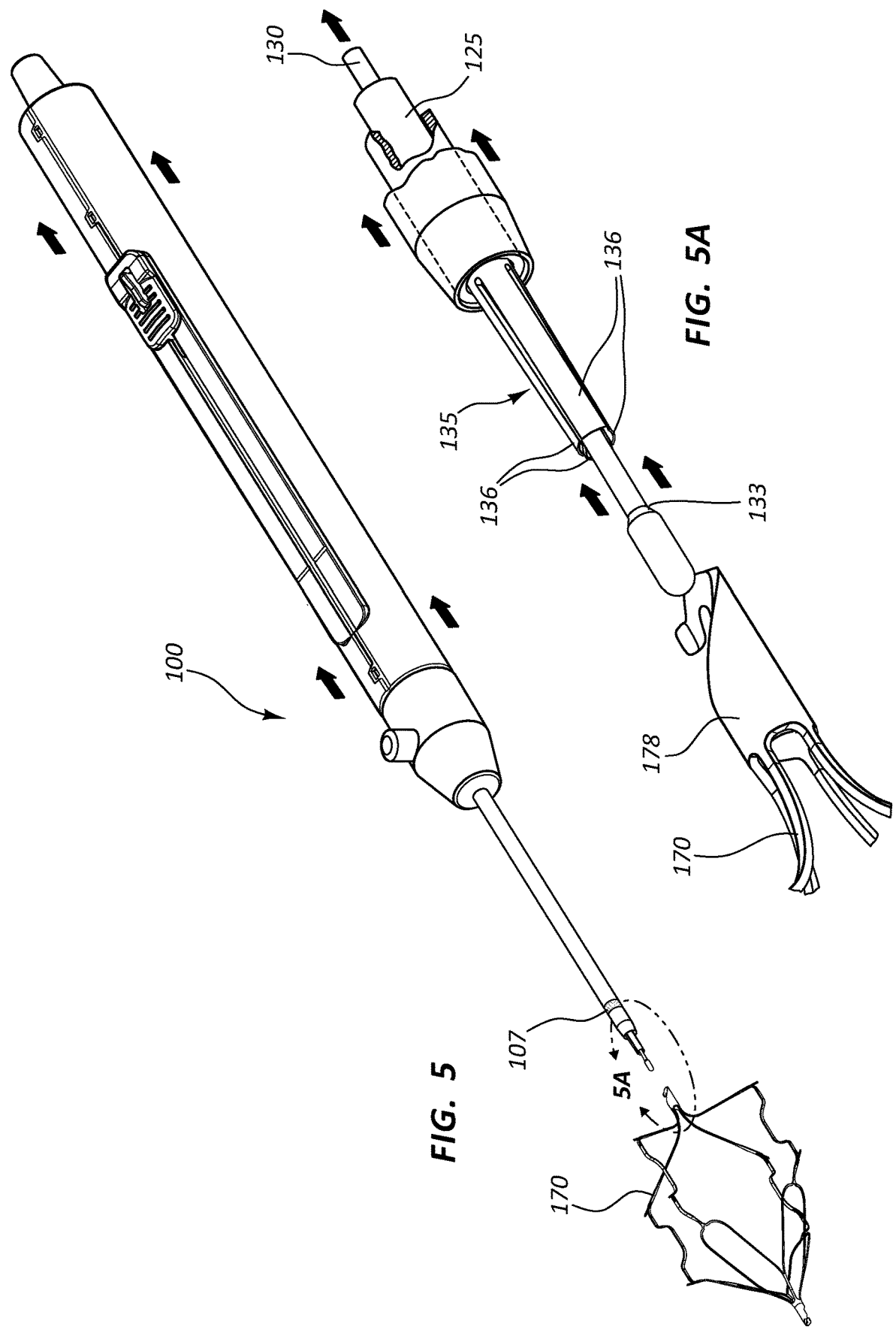

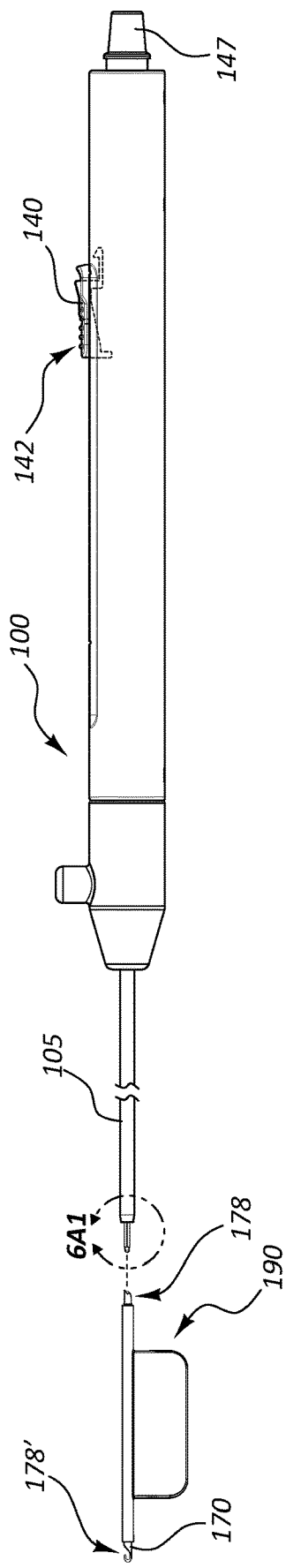
FIG. 6A
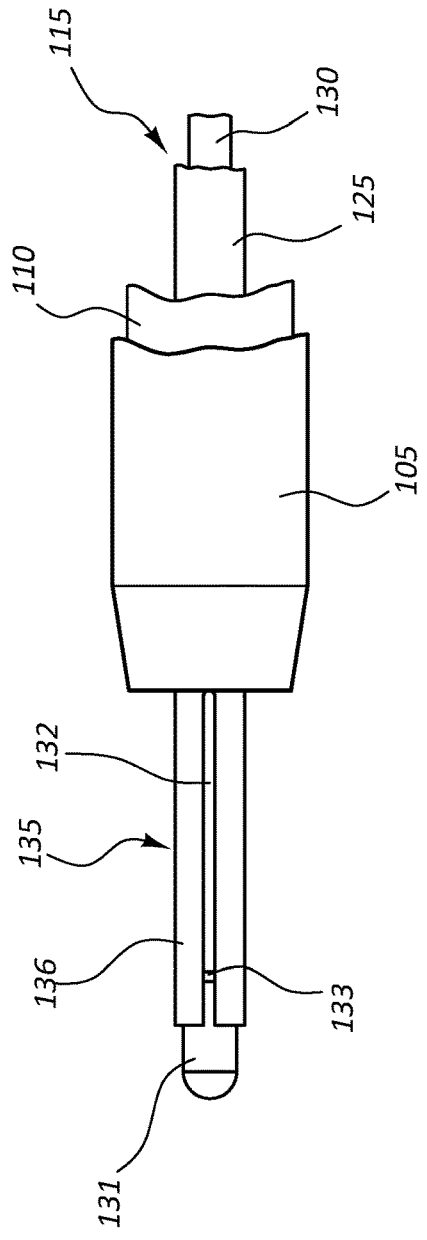
FIG. 6A1

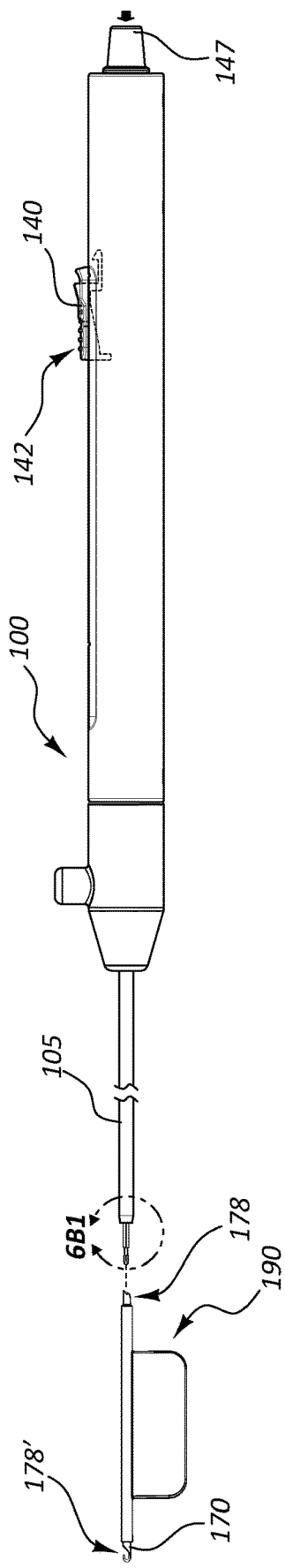
FIG. 6B
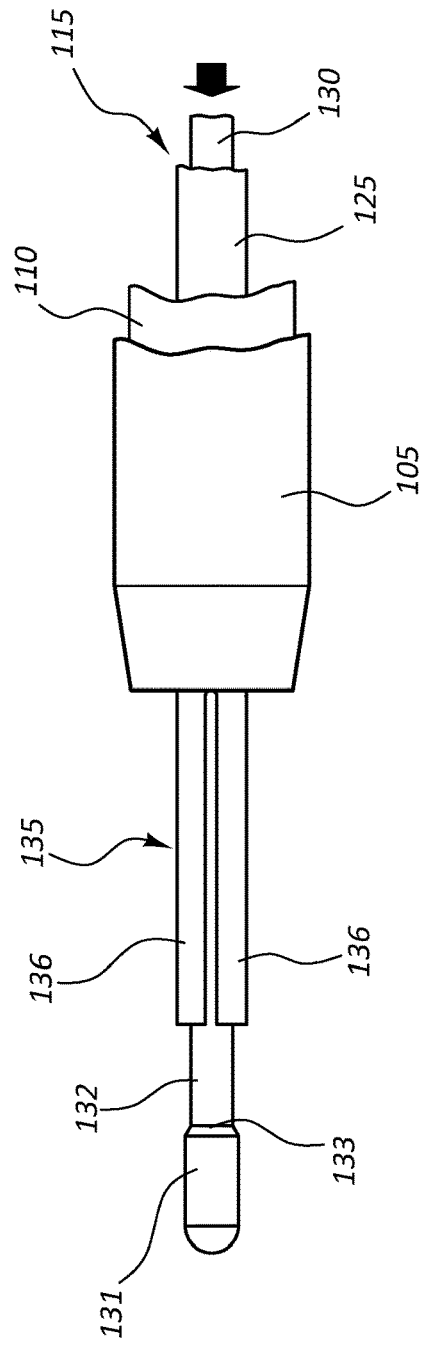
FIG. 6B1

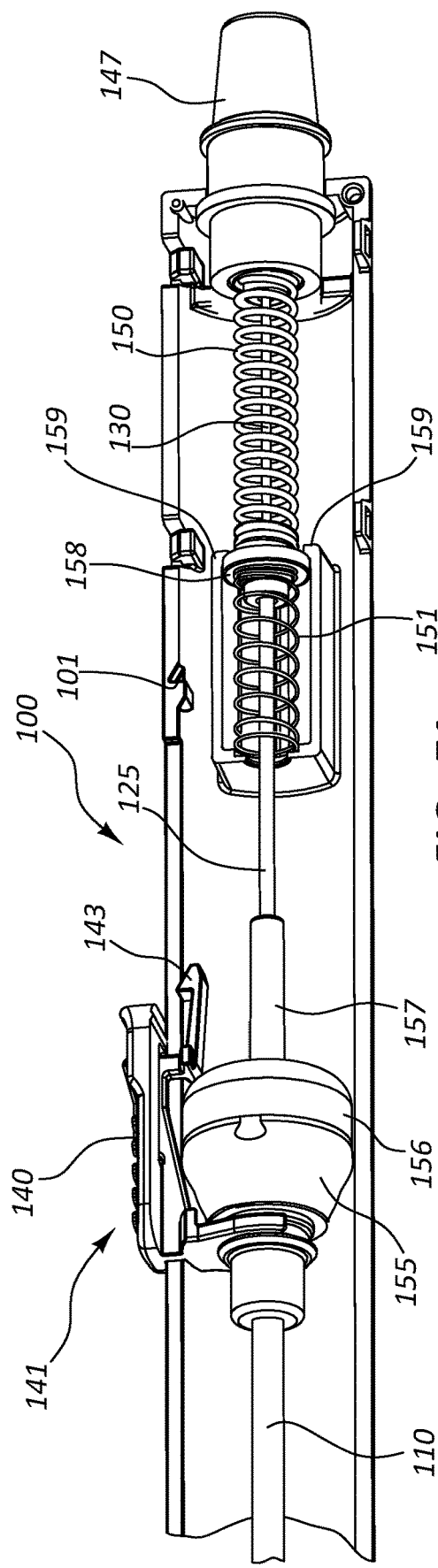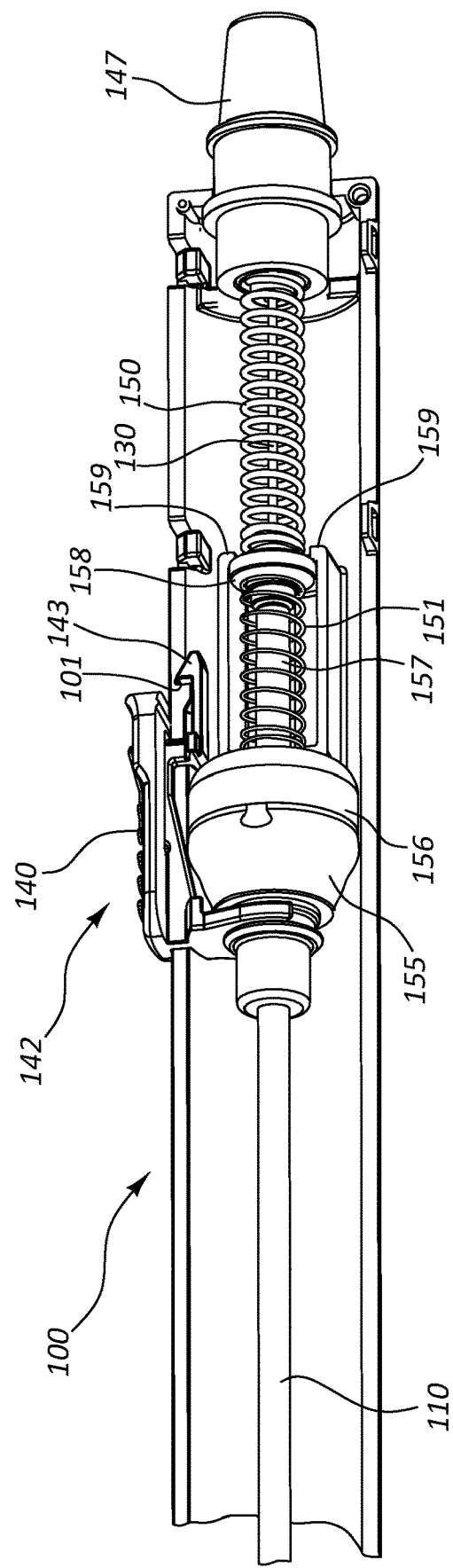
FIG. 7A
FIG. 7B

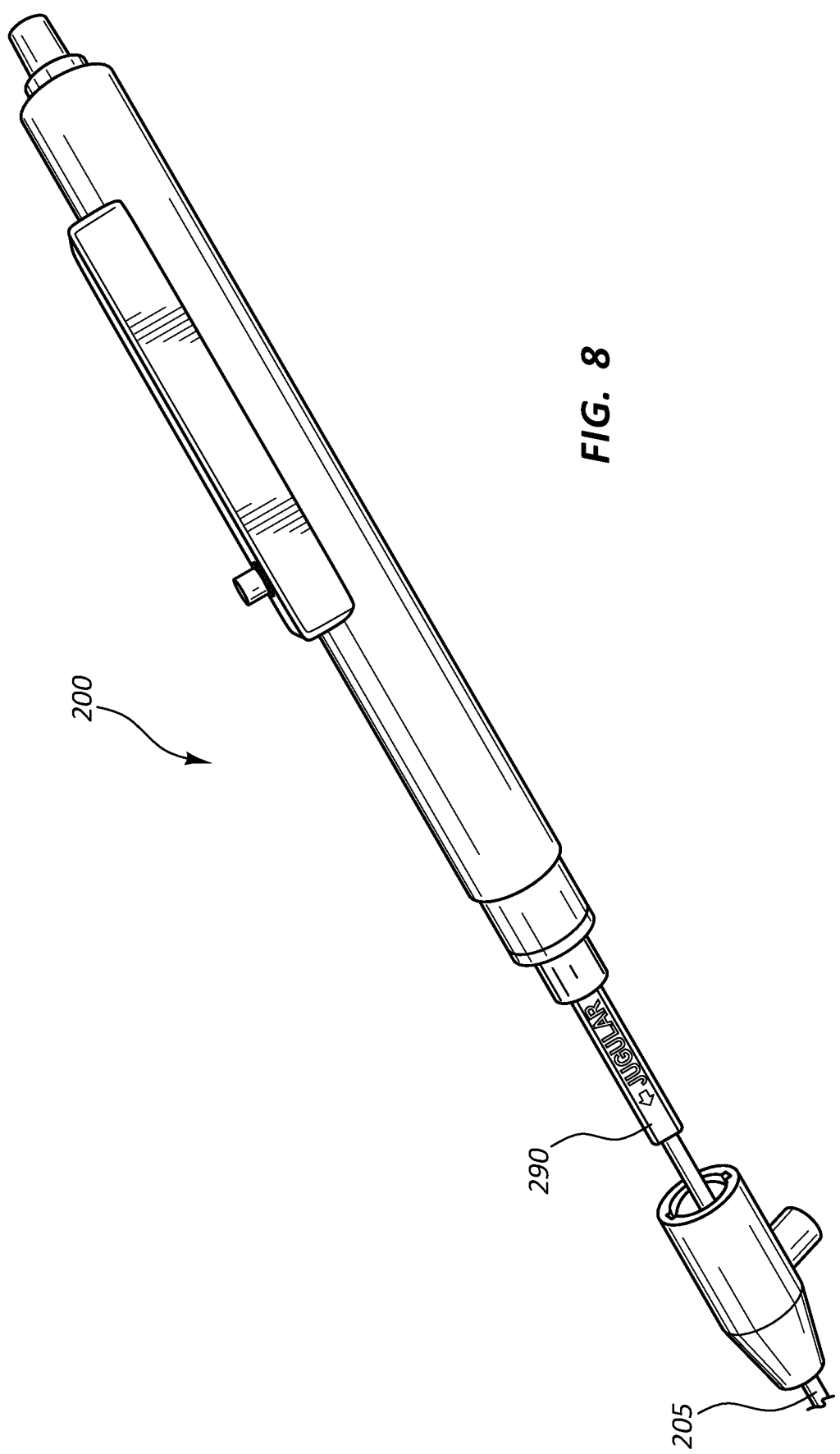

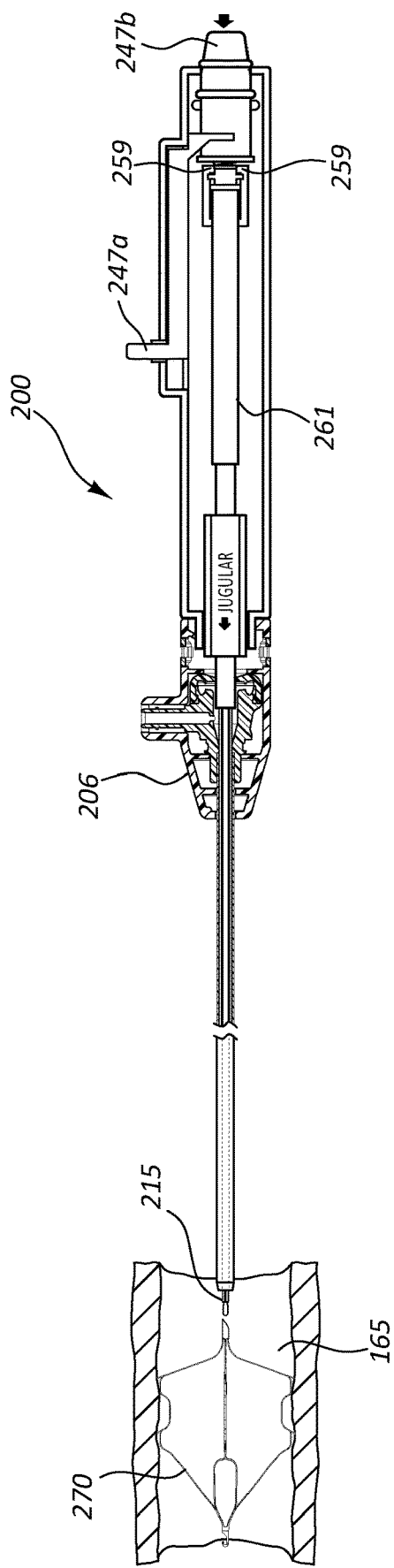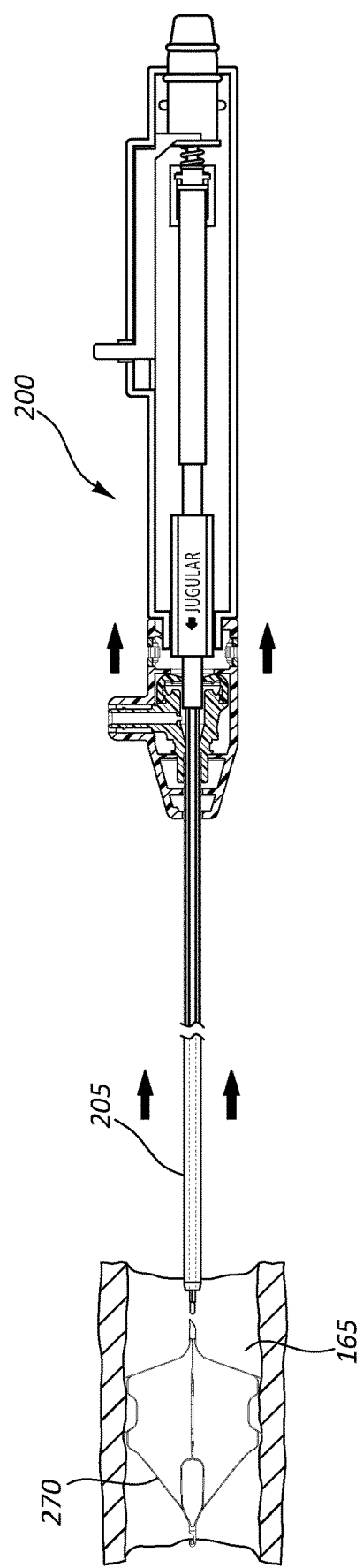
FIG. 9E
FIG. 9F

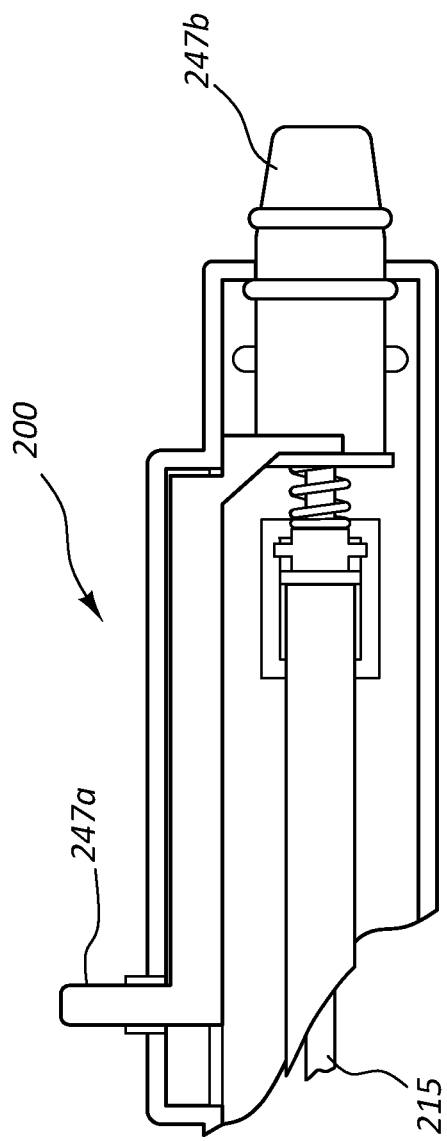
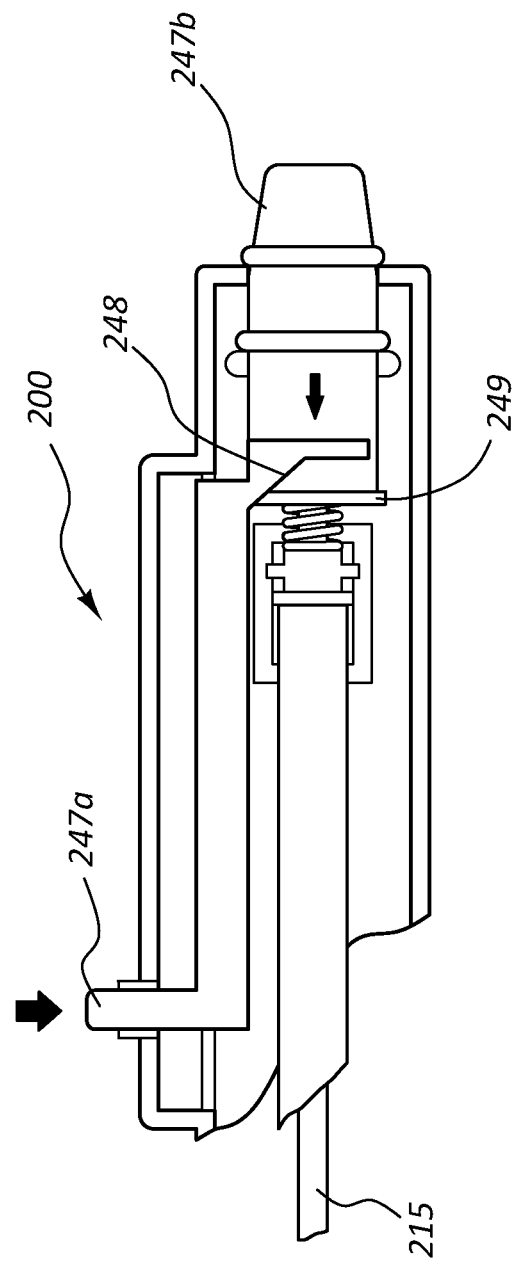
FIG. 10A
FIG. 10B

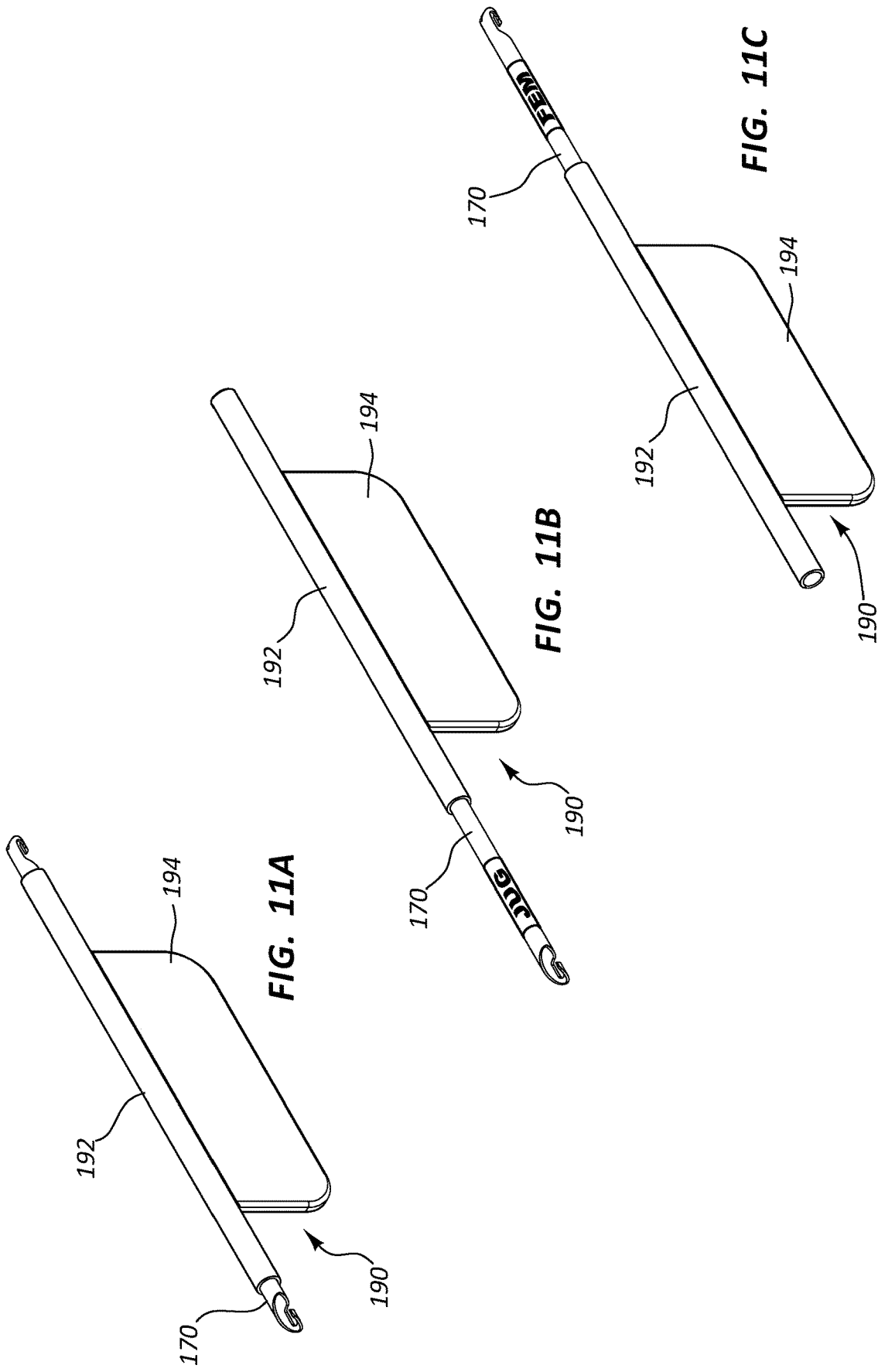

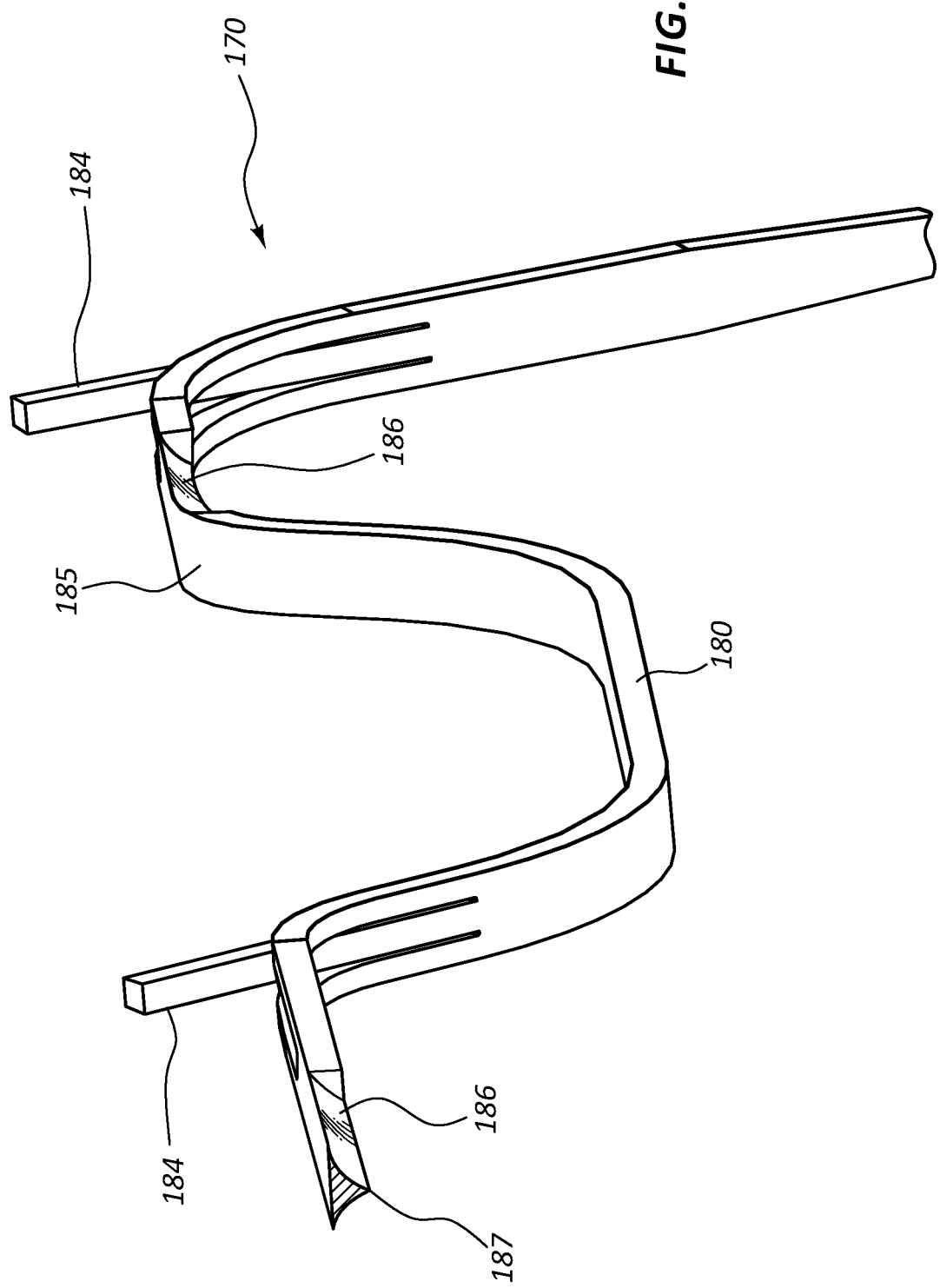

VASCULAR FILTER DELIVERY SYSTEMS AND METHODS

RELATED APPLICATIONS

This application claims priority to U.S. Provisional Application No. 61/863,993, filed on Aug. 9, 2013 and titled, "Vascular Filter Delivery Systems and Methods," which is hereby incorporated by reference in its entirety.

TECHNICAL FIELD

The present disclosure relates generally to filters configured to be disposed within a body lumen and to systems and methods for delivering filters configured to be disposed within a body lumen. More particularly, the present disclosure relates to filters or similar devices that may be configured to capture blood clots within the vasculature and to delivery devices configured to dispose filters within the vasculature, such as within the inferior vena cava. Some filters may have a surface with a sharp edge configured to ease filter removal, and some devices may have mechanisms for limiting inadvertent decoupling of filters.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 4 is a perspective view of the filter deployment device of FIG. 1, wherein the filter is in a deployed configuration.

FIG. 4A is a detail view, taken around line 4A, of a portion of the filter deployment device and filter of FIG. 4.

FIG. 5 is a perspective view of the filter deployment device of FIG. 1, wherein the filter is in a deployed configuration and decoupled from the filter deployment device.

FIG. 5A is a detail view, taken around line 5A, of a portion of the filter deployment device and filter of FIG. 5.

FIG. 6A is a side view of a filter deployment device assembly in a first configuration.

FIG. 6A1 is a detail view, taken around line 6A1, of a portion of the filter deployment device of FIG. 6A.

FIG. 6B is a side view of a filter deployment device assembly in a second configuration.

FIG. 6B1 is a detail view, taken around line 6B1, of a portion of the filter deployment device of FIG. 6B.

FIG. 7A is a side view of a locking or safety mechanism of a filter deployment device in a first configuration.

FIG. 7B is a side view of a locking or safety mechanism of a filter deployment device in a second configuration.

FIG. 8 is a perspective view of another embodiment of a filter deployment device, comprising another embodiment of a locking or safety mechanism.

FIG. 9E is a partial cross-sectional side view of the filter deployment device of FIG. 8 depicting the locking or safety mechanism in a fifth configuration.

FIG. 9F is a partial cross-sectional side view of the filter deployment device of FIG. 8 depicting the locking or safety mechanism in a sixth configuration.

FIG. 10A is a partial cross-sectional side view of a portion of the filter deployment device of FIG. 8, in the configuration of FIG. 9F.

FIG. 10B is a partial cross-sectional side view of a portion of the filter deployment device of FIG. 8, in the configuration of FIG. 9E.

FIG. 11A is a perspective view of a filter packaging cartridge.

FIG. 11B is a perspective view of a filter packaging cartridge in a first configuration.

FIG. 11C is a perspective view of a filter packaging cartridge in a second configuration.

FIG. 12B is a cross-sectional perspective view of a portion of the body lumen filter of FIG. 12A taken through line 12B-12B.

DETAILED DESCRIPTION

Figure 1:
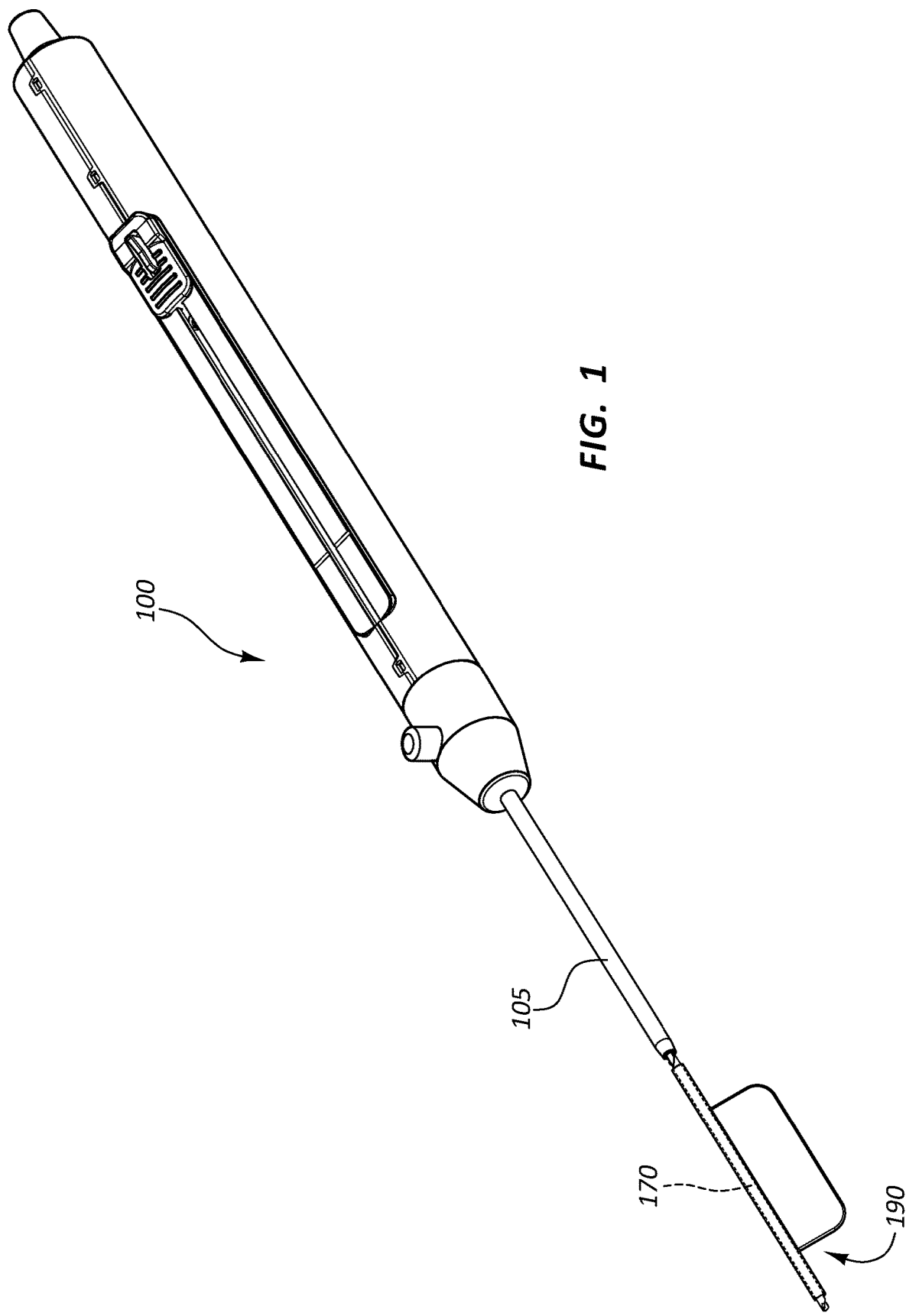
FIG. 1 is a perspective view of a filter deployment device coupled to a filter, wherein the filter is retained by a filter packaging cartridge.

A filter may be configured to be disposed within the vasculature to capture or trap material within a body lumen. For example, a filter may be configured to trap blood clots in the vasculature. In some embodiments, a filter may be disposed within the inferior vena cava and be configured to inhibit pulmonary embolism. Furthermore, some filters within the scope of this disclosure may be configured to be removable. Still further, in certain embodiments a filter according to this disclosure may be configured to slice through tissue ingrowth or tissue encapsulation during removal.

A filter deployment device or system may be configured to deliver a filter or filters to positions within a body lumen. For example, the filter may be disposed within the inferior vena cava. Furthermore, some filter deployment devices within the scope of this disclosure may be configured to limit inadvertent decoupling of a filter. Still further, certain filter deployment devices may be configured to retrieve a deployed filter, as further detailed below.

Though many of the examples provided herein may refer to a filter disposed within the inferior vena cava or a device for disposing a filter within the inferior vena cava, the present disclosure is applicable to a variety of filters configured to be disposed elsewhere within the vasculature or within other body lumens and to devices for delivering filters and other medical appliances to be disposed elsewhere within the vasculature or within other body lumens.

It will be readily understood by one of skill in the art having the benefit of this disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. With respect to deployment devices disclosed herein, the proximal end refers to the end nearest a practitioner when the device is in use.

Further, as used herein "deployed" or "deployed state" refers to a filter in an expanded configuration, such as a radially expanded configuration, for example, wherein the filter is unsheathed. An undeployed filter may thus comprise a filter in a radially restrained configuration such as within a sheath. To "deploy" a filter may comprise unsheathing or otherwise transitioning a filter from an undeployed configuration to a deployed configuration, A deployed filter, however, may or may not be coupled to a filter deployment device. Thus, filter deployment or manipulation devices within the scope of this disclosure may be configured to deploy a filter independent of whether the filter is otherwise coupled to the deployment or manipulation device. For example, a deployed filter may be in an expanded or unsheathed configuration while still coupled to a portion of a filter deployment device.

FIG. 1 is a perspective view of a filter deployment device 100 coupled to a filter 170, wherein the filter 170 is in a radially restrained packaged configuration disposed within a filter packaging cartridge 190. As illustrated, the filter 170 is coupled to the filter deployment device 100 at or adjacent a distal end of an introducer sheath 105. It will be appreciated by one skilled in the art having the benefit of this disclosure that the filter deployment device described herein may be used in connection with other filters or devices in addition to the exemplary filter illustrated in this or any other figure.

Figure 2:
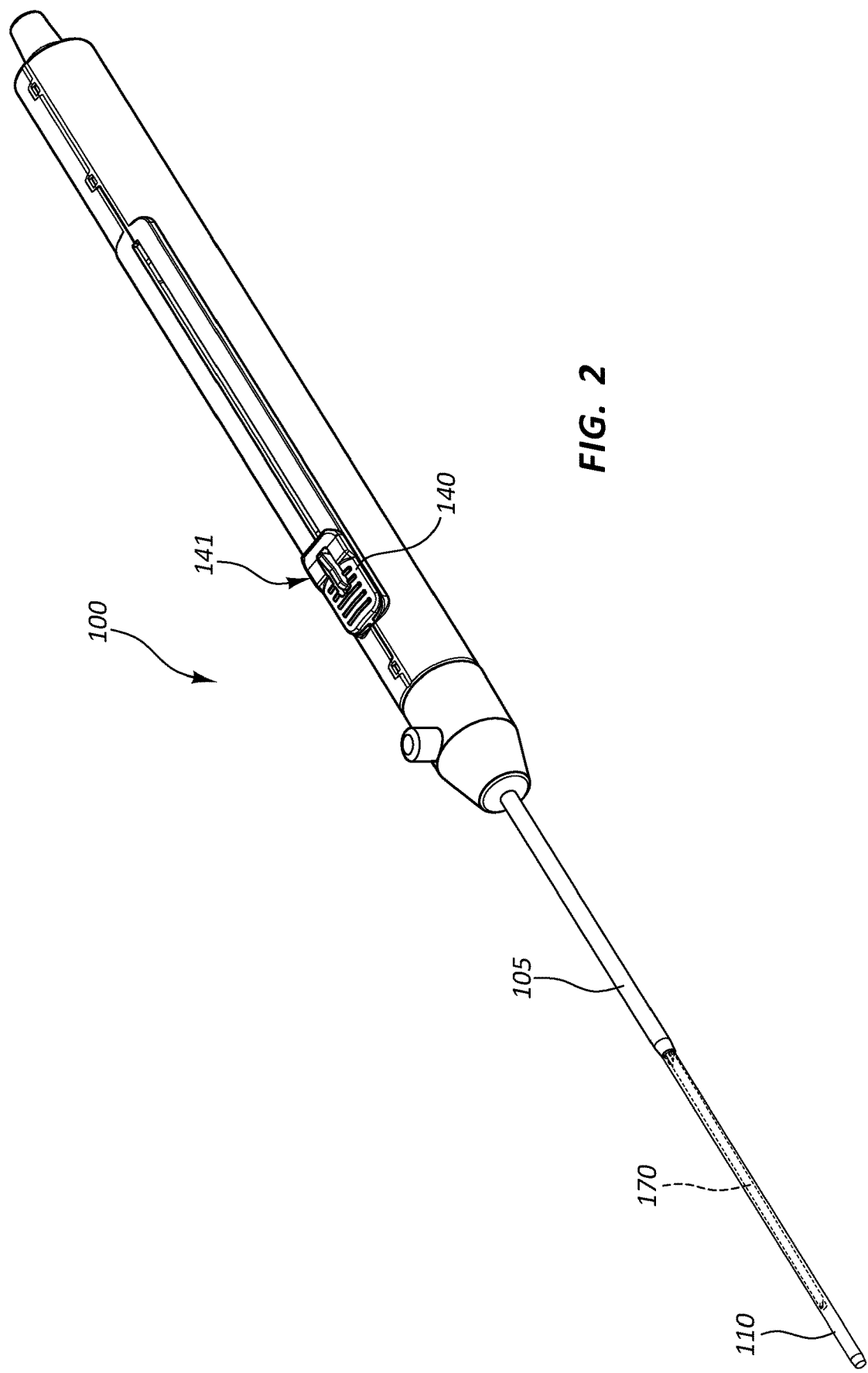
FIG. 2 is a perspective view of the filter deployment device of FIG. 1, wherein the filter is disposed within a delivery sheath.

FIG. 2 is a perspective view of the filter deployment device 100 of FIG. 1, with the filter packaging cartridge removed, and the filter 170 in a radially restrained configuration within a delivery sheath 110. In some embodiments, the filter 170 may be partially disposed within the delivery sheath 110 while partially disposed in a radially restrained configuration. In other words, a portion of a filter, such as filter 170, may be deployed from a delivery sheath, such as delivery sheath 110, while another portion of the filter is radially restrained within the delivery sheath 110. In the illustrated embodiment, the filter 170 is completely disposed within the delivery sheath 110. The delivery sheath 110 may be axially disposed within the introducer sheath 105. The delivery sheath 110 may be configured to retain the filter 170, or a portion of the filter 170, in the radially restrained configuration.

Figures 3, 3A:
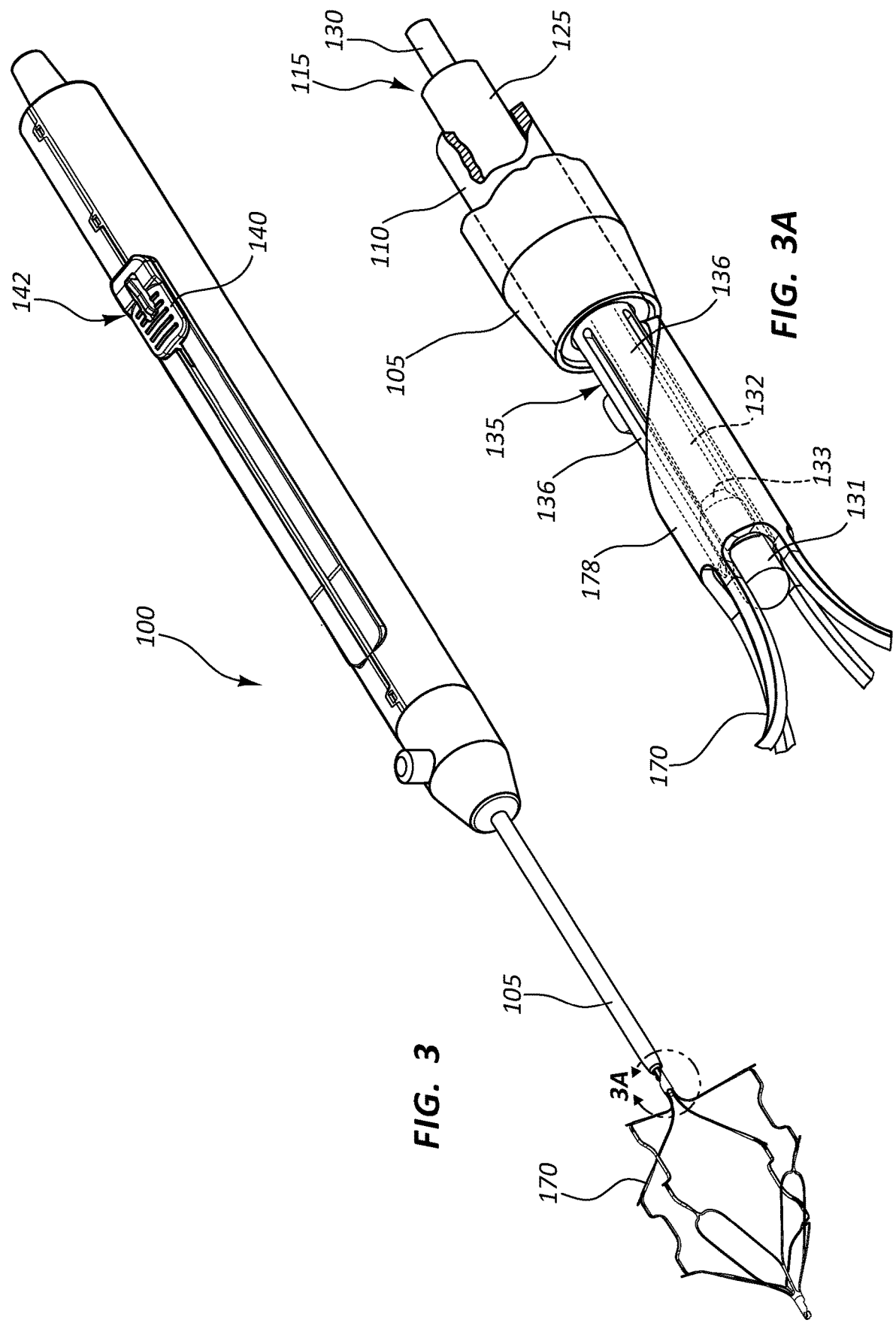
FIG. 3 is a perspective view of the filter deployment device of FIG. 1, wherein the filter is in a deployed configuration.
FIG. 3A is a detail view, taken around line 3A, of a portion of the filter deployment device and filter of FIG. 3.

FIG. 3 is a perspective view of the filter deployment device 100 of FIG. 1, wherein the delivery sheath is in a retracted configuration with respect to the filter 170, and the filter 170 is in a radially expanded deployed configuration. Also, in the illustrated embodiment, the filter 170 is coupled to the filter deployment device 100. In the illustrated embodiment, the delivery sheath is fully retracted within the introducer sheath 105. In other embodiments, the delivery sheath may only be partially retracted within the introducer sheath 105 when the filter 170 is fully or partially deployed.

FIG. 3A is a detail view, taken around line 3A, of a portion of the filter deployment device 100 and filter 170 of FIG. 3. FIG. 3A illustrates a portion of the filter deployment device 100 wherein the filter 170 may be coupled to the filter deployment device 100. As illustrated in FIG. 3A, the filter deployment device 100 may comprise an introducer sheath 105, a delivery sheath 110 axially displaceable within the introducer sheath 105, a deployment member 115 axially displaceable within the delivery sheath 110, and a filter coupling mechanism disposed adjacent a distal end of the deployment member 115. The filter coupling mechanism may be configured to releasably couple the filter 170 to the deployment member 115 independent of the relative position of the delivery sheath 110. For example, the filter coupling mechanism may couple the filter 170 regardless of the position of the delivery sheath 110. Stated another way, the filter 170 may be coupled to the filter coupling mechanism whether the filter 170 is in a deployed and/or expanded configuration or whether the filter 170 is in a packaged, sheathed, and/or undeployed configuration.

In embodiments, the deployment member 115 and the filter coupling mechanism may be configured to proximally and/or distally displace the filter 170 independent of the position of the filter 170 with respect to the delivery sheath 110. In other embodiments, the deployment member 115 and the filter coupling mechanism may be configured to proximally and/or distally displace the filter 170 when the filter 170 is disposed outside the delivery sheath 110. For example, a user may proximally and/or distally displace the filter 170 to dispose the filter 170 in a desired location and/or position, such as in the inferior vena cava. For example, proximal or distal displacement of the deployment member 115 within a body lumen may correspond to proximal or distal displacement of the filter 170 within the lumen due to the coupling of the filter 170 to the deployment member 115.

In the illustrated embodiment, the filter coupling mechanism comprises a distal portion of an outer member 125, wherein the distal portion of the outer member 125 may be configured to releasably couple the filter 170. The filter coupling mechanism further comprises a distal portion of an inner member 130 disposed within the distal portion of the outer member 125. In some embodiments, the inner member 130 may be axially displaceable within the outer member 125. In some such embodiments, displacement of the inner member 130 with respect to the outer member 125 may be configured to selectively couple the filter 170 to the distal portion of the outer member 125. For example, the distal portion of the outer member 125 may be coupled to the filter 170 at a first end of the filter 170, or the distal portion of the outer member 125 may be coupled to the filter 170 at a second end of the filter 170. Thus, in some embodiments, the filter 170 may be configured such that it may be coupled to the filter deployment device at either the first end or the second end of the filter 170.

In some embodiments, the filter coupling mechanism may comprise an outer member 125 configured to selectively engage or couple a filter 170. The filter coupling mechanism may further comprise an actuating member, such as the inner member 130, which may be axially displaceable with respect to the outer member 125. Displacement of the actuating member with respect to the outer member 125 may be configured to selectively couple the filter 170 to the outer member 125.

Referring again to FIG. 3A, in the illustrated embodiment, the outer member 125 comprises a collet 135 adjacent a distal end of the outer member 125. The collet 135 may be configured to releasably couple the filter 170 to the outer member 125. As illustrated, the collet 135 comprises a plurality of flexible legs 136. Specifically, in the illustrated embodiment, the collet 135 comprises four legs 136. In other embodiments, the collet 135 may comprise more or less than four legs 136.

The inner member 130 may comprise a proximal section, a middle section 132, and a distal section 131. In certain embodiments, the distal section 131 may be configured to engage the collet 135. As illustrated, the distal section 131 of the inner member 130 comprises an outside diameter that is greater than an outside diameter of the middle section 132.

Distal displacement of the inner member 130 with respect to the collet 135 may be configured to decouple a filter 170 from the outer member 125. For example, in the configuration shown in FIG. 3A the distal section 131 of the inner member 130 may tend to bias the legs 136 of the collet 135 into contact with a portion of the filter 170. As further outlined below, this interaction may tend to couple the collet 135 to the filter 170 due to friction between these components. Distal displacement of the inner member 130 with respect to the collet 135 may remove the bias as the middle section 132 of the inner member 130 has a smaller diameter than the distal section 131. As illustrated, the inner member 130 further comprises an annular taper 133 disposed between the distal section 131 and the middle section 132 of the inner member 130. The annular taper 133 may be configured to engage an inside surface of the collet 135 such that a portion of the collet 135, such as the legs 136, is thus biased radially outward when the collet 135 is in a filter coupling configuration. Stated another way, the legs 136 of the collet 135 may be displaced radially outward exerting a force on the filter 170. The force may couple the filter 170 to the outer member 125, for example, due to friction.

When coupling the filter 170 to the collet 135, the annular taper 133 may be retracted toward the collet 135 and upon engagement between the annular taper 133 and the legs 136 of the collet 135, the legs 136 may be biased, extended, and/or pushed radially outward from a central longitudinal axis of the outer member 125. The engagement between the annular taper 133 and the collet 135 may thus be configured to transition the collet 135 from a filter decoupling configuration, when not biased radially outward, to a filter coupling configuration. In the filter decoupling configuration, the filter 170 may be decoupled and/or released from the filter deployment device. In contrast, in the filter coupling configuration the filter 170 may be coupled and/or attached to the filter deployment device. In other embodiments, the annular taper 133 may be configured to disengage from the inside surface of the collet 135 such that the legs 136 of the collet 135 are not biased radially outward and/or tend to invert radially inward toward the central longitudinal axis of the outer member 125 such that the diameter of at least a portion of the collet 135 may decrease. The disengagement of the annular taper 133 from the outer member 125 may be configured to transition the collet 135 from a filter coupling configuration to a filter decoupling configuration. Any suitable mechanism for engaging the inner member 130 with the outer member 125 is also within the scope of this disclosure.

In some embodiments, an inner member may thus exert a radially outward biasing force to couple a filter to a filter deployment device. In another embodiment, a collet may be configured to extend around and/or over at least a portion of a filter to couple the filter to the outer member. A secondary member may tend to bias the collet radially inward to couple the filter in embodiments wherein the collet extends over the filter.

As shown in FIGS. 3 and 3A, the collet 135 may be configured to releasably couple the outer member 125 to a tube portion 178 of the filter 170. The collet 135 may be further configured to be at least partially disposed within the tube portion 178. In the illustrated embodiment of FIG. 3A, an outside diameter of a portion of the collet 135 disposed within the tube portion 178 is biased into contact with an inside diameter of the tube portion 178, thus the filter coupling mechanism and/or the collet 135 is in the filter coupling configuration. When the legs 136 of the collet 135 are biased radially outward they may generate friction to couple the filter 170 to the outer member 125. In other embodiments, the portion of the collet 135 that may be disposed within the tube portion 178 may comprise an outside diameter wherein the outside diameter of the collet 135 may be less than the inside diameter of the tube portion 178. In such a configuration, the filter coupling mechanism and/or the collet 135 may be in a filter decoupling configuration.

In the filter coupling configuration, the filter coupling mechanism and/or the collet 135 may be configured to couple the outer member 125 to the filter 170. In the filter decoupling configuration, the filter coupling mechanism and/or the collet 135 may be configured to decouple the outer member 125 from the filter 170. Stated another way, the filter coupling mechanism and/or the collet 135 may not be configured to engage with and retain a filter 170 when the filter coupling mechanism and/or the collet 135 is in the filter decoupling configuration.

Referring again to FIG. 2, the filter deployment device 100 may further comprise a deployment actuator 140. In the illustrated embodiment, when the deployment actuator 140 is at or adjacent a first position 141, the filter 170 is sheathed by the delivery sheath 110. In this configuration, the filter 170 is in a radially restrained configuration within the delivery sheath 110. Referring again to FIGS. 3 and 3A, when the deployment actuator 140 is at or adjacent a second position 142 the delivery sheath 110 may be retracted to expose the filter 170, thus allowing radial expansion of the filter 170 to a deployed configuration. Thus, upon the retraction of the delivery sheath 110, the filter 170, as illustrated in FIG. 3, may be configured to deploy and/or expand. Stated another way, a delivery sheath 110 may be configured to retract to deploy a filter 170 disposed within the delivery sheath 110.

In some embodiments, a filter coupling mechanism may be configured to recouple a decoupled filter, such as a filter previously deployed and released within a body lumen, or to recouple a filter prior to introduction into the body. The filter coupling mechanism may be configured to recouple the decoupled filter at either a first end or a second end of the decoupled filter, or any other coupling location on a filter. A delivery sheath 110 may be configured to extend over the filter to dispose the recoupled filter within the delivery sheath 110. Disposition of the recoupled filter within the delivery sheath 110 may ease and/or facilitate removal of or repositioning of the recoupled filter from a body lumen. For example, a practitioner may first couple a filter within a body lumen to the filter deployment device 100, and then extend the delivery sheath 110 to withdraw the filter into an undeployed state. When sheathed, the filter may more readily be moved along a body lumen to withdraw the filter from the body or to adjust the position of the filter, for example.

A pathway through a body to and/or from a filter disposition location or site may be tortuous, thus a small filter profile, as found when the filter is in a packaged, sheathed, and/or undeployed configuration, may ease and/or facilitate filter disposition in and/or removal from a body lumen. Additionally, a practitioner may couple a filter disposed within a body lumen to the filter deployment device 100 and adjust the position of the filter within the lumen without extending the delivery sheath 110, for example if the desired amount of displacement is small. Similarly, a practitioner may partially extend the delivery sheath 110, to partially restrain expansion of the filter when adjusting the position of the filter.

FIG. 4 is a perspective view of the filter deployment device 100 of FIG. 1, wherein the delivery sheath is in a retracted configuration, the filter 170 is in a deployed configuration, and the filter coupling mechanism is configured to decouple the filter 170 from the filter deployment device 100. FIG. 4A is a detail view, taken around line 4A, of a portion of the filter deployment device 100 and the filter 170 of FIG. 4. FIG. 4A illustrates the portion of the filter deployment device with the filter coupling mechanism configured such that the filter 170 may be decoupled from the filter deployment device.

As illustrated, the inner member 130 is distally displaced with respect to the collet 135 such that the inner member 130 does not exert a radially outward biasing force on the collet 135. Thus, in the configuration shown, the inner member 130 and the collet 135 are configured to decouple the filter 170 from the distal portion of the outer member 125. Referring to FIG. 4A, the annular taper 133 is disengaged from the inside surface of the collet 135 such that the legs 136 of the collet 135 are not biased radially outward and/or are inverted radially inward toward the central longitudinal axis of the outer member 125 such that the diameter of at least a portion of the collet 135 has decreased. The disengagement of the annular taper 133 from the outer member 125 may be configured to transition the collet 135 from a filter coupling configuration to a filter decoupling configuration. Any suitable mechanism for engaging the inner member 130 with the outer member 125 is also within the scope of this disclosure.

In some embodiments, the collet 135 may be configured to releasably couple the outer member 125 to a tube portion 178 of the filter 170. The collet 135 may be further configured to be at least partially disposed within the tube portion 178 of the filter 170. In the illustrated embodiment of FIG. 4A, the portion of the collet 135 that is disposed within the tube portion 178 comprises an outside diameter wherein the outside diameter of the collet 135 is less than the inside diameter of the tube portion 178. In such a configuration, the filter coupling mechanism and/or the collet 135 may be in a filter decoupling configuration. As described above, in the filter decoupling configuration the filter coupling mechanism and/or the collet 135 may be configured to decouple the outer member 125 from the filter 170.

FIG. 5 is a perspective view of the filter deployment device 100 of FIG. 1, wherein the delivery sheath is in a retracted configuration, the filter 170 is in a deployed and/or expanded configuration, and the filter 170 is decoupled from the filter deployment device 100. FIG. 5A is a detail view, taken around line 5A, of a portion of the filter deployment device 100 and the filter 170 of FIG. 5. FIG. 5A illustrates the portion of the filter deployment device wherein the filter 170 is decoupled from the filter deployment device.

As illustrated, the inner member 130 may be distally displaced with respect to the collet 135 when the filter deployment device 100 is in the filter decoupling configuration, allowing the collet 135 to be withdrawn from the filter 170 and thereby decouple the filter 170 from the distal portion of the outer member 125. The arrows indicate that the filter deployment device 100 may be moving or has moved distally in relation to the filter 170 such that the decoupled filter 170 may remain in a body lumen, for example. Referring to FIG. 5A, the annular taper 133 is disengaged from the inside surface of the collet 135 such that the legs 136 of the collet 135 are not biased radially outward and/or are inverted radially inward toward the central longitudinal axis of the outer member 125 such that the diameter of at least a portion of the collet 135 has decreased. As illustrated, the disengagement of the annular taper 133 from the outer member 125 transitioned the collet 135 from a filter coupling configuration to a filter decoupling configuration. Any suitable mechanism for disengaging the inner member 130 from the outer member 125 is also within the scope of this disclosure.

The collet 135 may be configured to releasably couple the outer member 125 to a tube portion 178 of the filter 170. The collet 135 may be further configured to be at least partially disposed within the tube portion 178 of the filter 170. In the illustrated embodiment of FIG. 5A, the portion of the collet 135 that may have been disposed within the tube portion 178 comprises an outside diameter wherein the outside diameter of the collet 135 is less than the inside diameter of the tube portion 178. In the illustrated configuration, the filter coupling mechanism and/or the collet 135 is in a filter decoupling configuration. As described above, in the filter decoupling configuration the filter coupling mechanism and/or the collet 135 may be configured to decouple the distal portion of the outer member 125 from the filter 170. As discussed, the arrows of FIG. 5A indicate that the filter deployment device may be moving or has moved distally in relation to the filter 170 such that the decoupled filter 170 may remain in a body lumen.

In some embodiments, a filter deployment device may further comprise one or more radiopaque markers 107. The radiopaque marker may assist a user or users in disposing and/or placing a filter at a location within a body lumen. The radiopaque marker may also assist a user in recoupling and/or retrieving a decoupled filter from a location within a body lumen. In some embodiments, the radiopaque markers may comprise a band. For example, the band may completely surround a portion of the filter deployment device. In other embodiments, the radiopaque marker may only partially surround a portion of the filter deployment device. Other configurations of radiopaque markers are also contemplated. In other embodiments, the radiopaque markers may comprise gold, gold alloys, or any other radiopaque material or materials.

A filter deployment device assembly is also disclosed. As shown in FIG. 2, for example, a filter deployment device assembly may comprise a delivery sheath 110 and a filter 170 axially displaceable within the delivery sheath 110, wherein the filter 170 may be configured to deploy within a body lumen. As shown in FIGS. 3 and 3A, the assembly may further comprise a deployment member 115 axially displaceable within the delivery sheath 110, and a filter coupling mechanism disposed adjacent a distal end of the deployment member 115, wherein the filter coupling mechanism may be configured to releasably couple the filter 170 to the deployment member 115 independent of the delivery sheath 110. For example, the filter coupling mechanism may couple the filter 170 regardless of the position of the delivery sheath 110. Stated another way, the filter 170 may be coupled to the filter coupling mechanism whether the filter 170 is in a packaged, sheathed, and/or undeployed configuration or whether the filter 170 is in a deployed and/or an expanded configuration. The deployment member 115 and the filter coupling mechanism may be configured to proximally and/or distally displace the filter 170 independent of the position of the filter 170 with respect to the delivery sheath 110. In other embodiments, the deployment member 115 and the filter coupling mechanism may be configured to proximally and/or distally displace the filter 170 when the filter 170 is disposed outside the delivery sheath 110.

As described above and as illustrated in FIGS. 3 and 3A, the filter coupling mechanism of the assembly may comprise an outer member 125, wherein the outer member 125 may be configured to selectively engage or couple a filter 170. The filter coupling mechanism may further comprise an inner member 130 disposed within the outer member 125. In some embodiments, the inner member 130 may be axially displaceable within the outer member 125. In some such embodiments, the displacement of the inner member 130 with respect to the outer member 125 may be configured to selectively couple the filter 170 to the outer member 125. For example, the outer member 125 may be coupled to the filter 170 at a first end of the filter 170 or the outer member 125 may be coupled to the filter 170 at a second end of the filter 170. In embodiments, the filter 170 may be configured such that it may be coupled to the filter deployment device 100 at either the first end or the second end of the filter 170.

In some embodiments, the filter coupling mechanism may comprise an actuating member axially displaceable with respect to an outer member, such as the outer member 125. Displacement of the actuating member with respect to the outer member may be configured to selectively couple a filter to the outer member.

A kit comprising a filter deployment device assembly is also disclosed. The kit may comprise a delivery sheath 110, a filter 170, a deployment member 115, and a filter coupling mechanism (FIGS. 3 and 3A). The kit may be used by a practitioner or other user to deliver, deploy, and/or dispose a filter 170 within a body lumen.

Figure 12A:
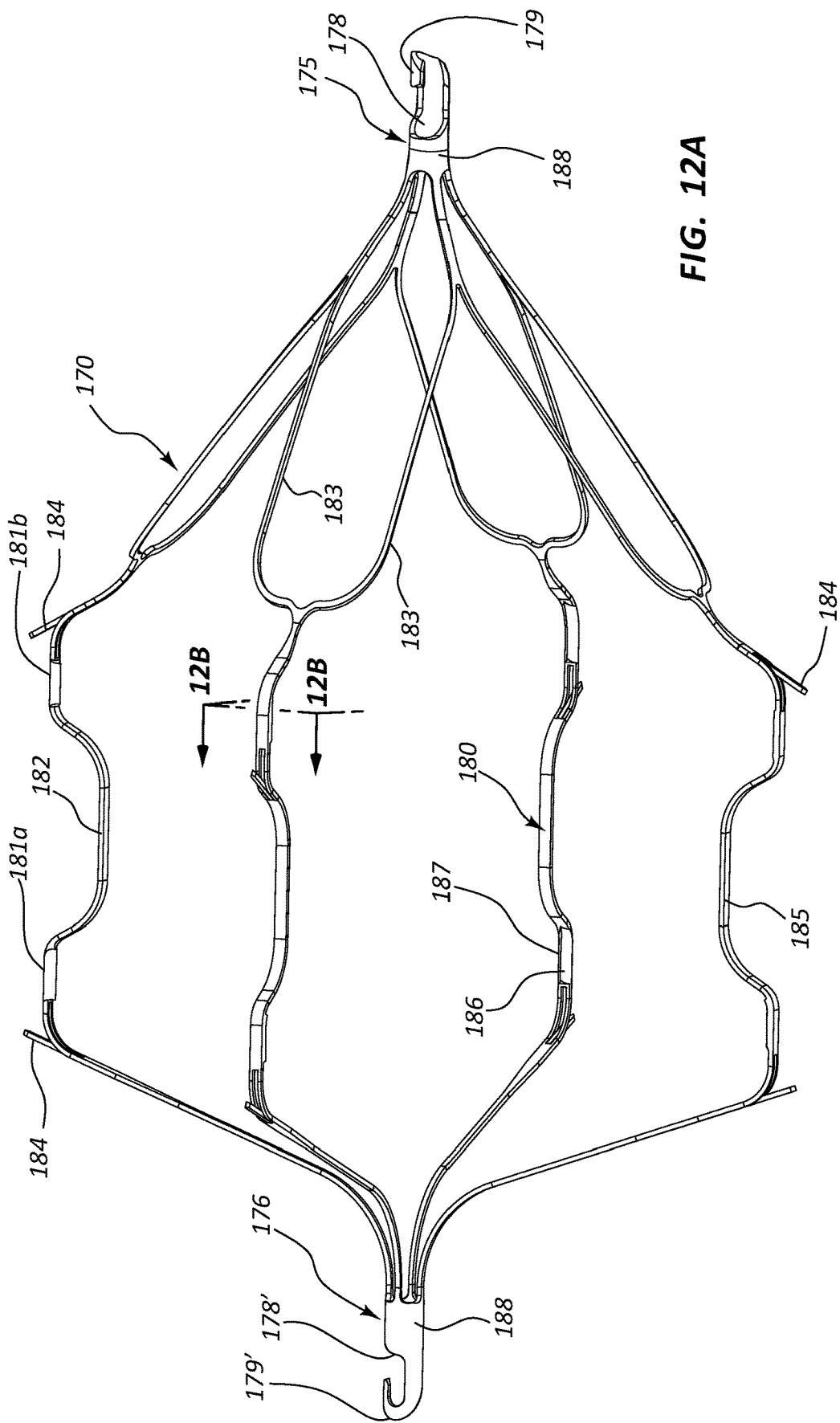
FIG. 12A is a side view of a body lumen filter.

An exemplary filter 170 is shown in FIG. 12A. This filter 170 may be used in connection with any of the devices, assemblies, kits, or other components disclosed herein. Further, it is within the scope of this disclosure to utilize any of these components with various filters of various types or designs. In the exemplary embodiment, the filter 170 may comprise a first axial portion 175 adjacent a first end of the filter 170, and a second axial portion 176 adjacent a second end of the filter 170. In some embodiments, at least one of the first and second axial portions 175, 176 may comprise a tube portion, for example tube portions 178 and 178', respectively. In other embodiments, at least one of the first and second axial portions 175, 176 may comprise a hook, for example hook portions 179 and 179', respectively. In one embodiment, a hook, such as hook 179 or 179', may be a secondary coupling mechanism. In some embodiments, the hook 179, 179' may allow and/or permit recoupling and/or removal of a decoupled filter. For example, a loop snare or other suitable medical device may be used to recouple, reposition, and/or remove a filter comprising one or more hooks 179, 179' from a body lumen. In yet another embodiment, at least one of the first and second axial portions 175, 176 may comprise both a tube portion 178, 178' and a hook 179, 179'. Other configurations of tube portions and/or hooks are also within the scope of this disclosure, including embodiments wherein a filter comprises only one such feature or comprises multiple hooks and/or tubes. Furthermore, the filter coupling mechanism may be configured to releasably couple the deployment member to either one of the first axial portion 175 or the second axial portion 176 of the filter 170.

The outer member 125 may comprise a collet 135 adjacent a distal end of the outer member 125, as discussed regarding the filter deployment device above and as shown in FIGS. 3 and 3A. The collet 135 may be configured to releasably couple the filter 170 to the outer member 125. The collet 135 may comprise a plurality of flexible legs 136. In some embodiments, the collet 135 may comprise four legs 136. In other embodiments, the collet 135 may comprise more or less than four legs 136.

As illustrated in FIGS. 3 and 3A, the inner member 130 may comprise a proximal section, a middle section 132, and a distal section 131. In certain embodiments, the distal section 131 may be configured to engage the collet 135. For example, the distal section 131 may be enlarged, comprising a diameter that is greater than an inside diameter of the outer member 125. The distal section 131 of the inner member 130 may comprise an outside diameter that is greater than an outside diameter of the middle section 132. In embodiments, distal displacement of the inner member 130 with respect to the collet 135 may be configured to decouple a filter 170 from the outer member 125.

In some embodiments, the inner member 130 may further comprise an annular taper 133 disposed between the distal section 131 and the middle section 132 of the inner member 130. In some such embodiments, the annular taper 133 may be configured to engage an inside surface of the collet 135 such that a portion of the collet 135 is biased radially outward when the collet 135 is in a filter coupling configuration. For example, the annular taper 133 may be retracted toward the collet 135 and upon engagement between the annular taper 133 and the flexible legs 136 of the collet 135 the legs 136 may be biased, extended, and/or pushed radially outward from a longitudinal axis of the outer member 130. The engagement between the annular taper 133 and the collet 135 may thus be configured to transition the collet 135 from a filter decoupling configuration to a filter coupling configuration. In the filter decoupling configuration the filter 170 may be decoupled and/or removed from the filter deployment device 100. In contrast, in the filter coupling configuration the filter 170 may be coupled and/or attached to the filter deployment device 100. In other embodiments, the annular taper 133 may be configured to disengage from the inside surface of the collet 135 such that the flexible legs 136 of the collet 135 are not biased radially outward and/or invert radially inward toward the longitudinal axis of the outer member 130 such that the diameter of the collet 135 may decrease. The disengagement of the annular taper 133 from the outer member 125 may be configured to transition the collet 135 from a filter coupling configuration to a filter decoupling configuration. Any suitable mechanism for engaging the inner member 130 with the outer member 125 is also within the scope of this disclosure.

The collet 135 may be configured to releasably couple the outer member 125 to a tube portion 178 of the filter 170 (see FIGS. 3 and 3A). The collet 135 may be further configured to be at least partially disposed within the tube portion 178 of the filter 170. In some embodiments, an outside diameter of a portion of the collet 135 disposed within the tube portion 178 is biased into contact with an inside diameter of the tube portion 178, thus the filter coupling mechanism is in the filter coupling configuration. In other embodiments, the portion of the collet 135 that may be disposed within the tube portion 178 may comprise an outside diameter wherein the outside diameter of the collet 135 may be less than the inside diameter of the tube portion 178. In such a configuration, the filter coupling mechanism and/or the collet 135 may be in a filter decoupling configuration. In the filter coupling configuration the filter coupling mechanism and/or the collet 135 may be configured to couple the outer member 125 to the filter 170. In the filter decoupling configuration, the filter coupling mechanism and/or the collet 135 may be configured to decouple the outer member 125 from the filter 170. In other words, the filter coupling mechanism and/or the collet 135 may be configured to not couple a filter 170 when the filter coupling mechanism and/or the collet 135 is in the filter decoupling configuration.

In one embodiment, as discussed above and as illustrated in FIG. 2, when a deployment actuator 140 is disposed at or adjacent the first position 141 the filter 170 is sheathed by the delivery sheath 110. In this embodiment, the filter 170 is in a packaged and/or undeployed configuration. In another embodiment, as shown in FIGS. 3 and 3A, when the deployment actuator 140 is disposed at or adjacent the second position 142 the delivery sheath 110 is retracted, exposing the filter 170 adjacent a distal end of the delivery sheath 110. Upon the retraction of the delivery sheath 110 the filter 170 may be configured to deploy and/or expand.

The filter coupling mechanism may be configured to recouple a decoupled filter. The filter coupling mechanism may be configured to recouple a decoupled filter 170 at either the first axial portion 175 or the second axial portion 176 of the filter 170 (FIG. 12A). The delivery sheath 110 may be further configured to extend to dispose the recoupled filter 170 within the delivery sheath 110 (FIG. 2). Disposition of the recoupled filter may ease and/or facilitate removal of the recoupled filter from a body lumen. A pathway through a body to a filter disposition location or site may be tortuous, thus a small filter profile, as found when the filter is in a packaged, sheathed, and/or undeployed configuration, may ease and/or facilitate filter removal from a body lumen.

In yet other embodiments, as described for the filter deployment device above, the filter deployment device assembly may further comprise one or more radiopaque markers 107 (FIG. 5). In other embodiments, the filter may comprise one or more radiopaque markers. The radiopaque markers may be configured to assist a user in disposing and/or placing a filter at a predetermined or other location within a body lumen. In some embodiments, the radiopaque markers may comprise a band. The band may completely surround a portion of the filter deployment device and/or filter. In other embodiments, the radiopaque marker may only partially surround a portion of the filter deployment device and/or filter. Other configurations of radiopaque markers are also contemplated. The radiopaque markers may comprise gold, gold alloys, or any other radiopaque material or materials.

FIGS. 6A and 6B are side views of a filter deployment device assembly in a first and a second configuration, respectively. The illustrated assembly comprises a filter 170 retained by a filter packaging cartridge 190, a filter coupling mechanism, an introducer sheath 105, a filter deployment device 100, a deployment actuator 140, and a coupling mechanism, such as coupling actuator 147. As discussed above, the filter deployment device assembly may be used with other filters or devices in addition to the exemplary filter disclosed herein. FIGS. 6A1 and 6B1 are detail views, taken around lines 6A1 and 6B1, respectively, of a portion of the filter deployment device assembly of FIGS. 6A and 6B, respectively. FIGS. 6A1 and 6B1 illustrate a filter coupling mechanism of the filter deployment device wherein the filter may be coupled to the filter deployment device. As illustrated in FIGS. 6A1 and 6B1, the filter deployment device comprises an introducer sheath 105, a delivery sheath 110 axially disposed within the introducer sheath 105, and a deployment member 115 axially disposed within the delivery sheath 110, wherein the deployment member 115 comprises an outer member 125 and an inner member 130 axially disposed within the outer member 125.

The deployment member 115 further comprises a filter coupling mechanism adjacent a distal end of the deployment member 115. The filter coupling mechanism comprises a collet 135 disposed at a distal portion of the outer member 125, and an enlarged distal end, corresponding to the distal section, 131 of the inner member 130. As illustrated, the inner member 130 further comprises an annular taper 133 disposed between the enlarged distal end 131 of the inner member 130 and a middle section 132 of the inner member 130. In some embodiments, engaging the annular taper 133 of the inner member 130 with the collet 135 may bias radially outward a plurality of legs 136 of the collet 135 such that a diameter of the collet 135 increases and the collet 135 engages a tube portion of a filter. As depicted in FIG. 6B1, the annular taper 133 may be disengaged from the collet 135 such that a diameter of the collet 135 decreases and the collet 135 disengages a tube portion of a filter.

Referring to FIGS. 6B and 6B1, actuation of the coupling actuator 147 (indicated by the arrows) may distally displace the enlarged distal end 131 of the inner member 130 relative to the collet 135 of the outer member 125. As described above, disengagement of the enlarged distal end 131 from the collet 135 allows and/or permits a plurality of flexible legs 136 of the collet 135 to bias and/or invert radially inward toward a central longitudinal axis of the outer member 125 such that a diameter of at least a portion of the collet 135 decreases, and the tube portion 178 of the filter 170 may be disposed around the filter coupling mechanism. Stated another way, the filter 170 may be coupled to the filter deployment device 100 at a distal end of the filter deployment device 100 by disposing a tube portion 178 of the filter 170 around the filter coupling mechanism when the filter coupling mechanism is in a filter coupling configuration.

Thus, as shown in FIGS. 6A and 6B, an exemplary procedure may comprise actuating a coupling actuator 147 to transition a filter coupling mechanism from a filter coupling configuration to a filter decoupling configuration. The exemplary procedure may further comprise disposing a tube portion 178 of a filter 170 over and/or around the filter coupling mechanism in the filter decoupling configuration. The coupling actuator 147 may then be released to couple the filter 170 to the filter deployment device 100.

Figure 6C:
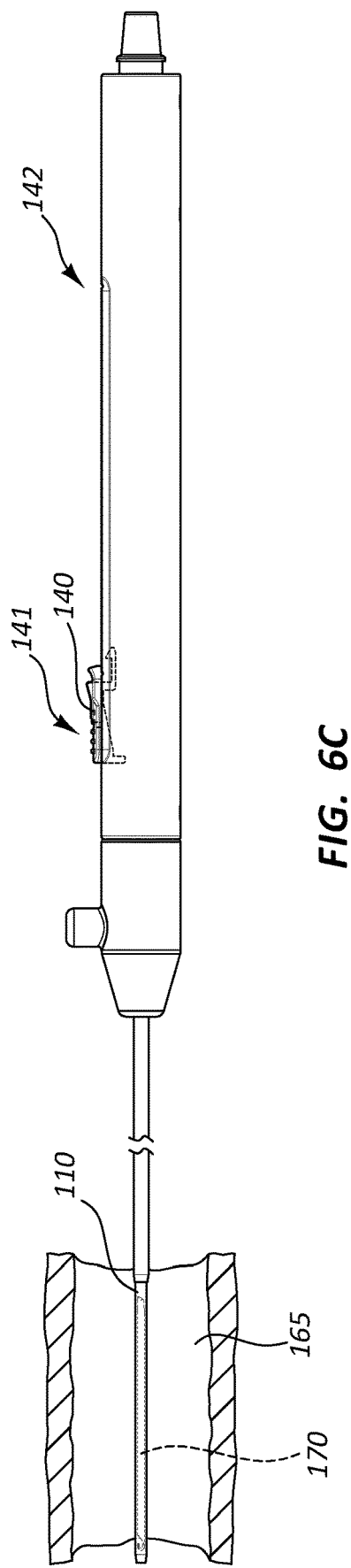
FIG. 6C is a side view of a filter deployment device assembly in a third configuration.

FIG. 6C is a side view of the filter deployment device assembly in a third configuration. As illustrated, in some procedures, the deployment actuator 140 may be actuated to extend the delivery sheath 110 over the coupled filter 170. In the illustrated embodiment, the coupled and sheathed filter 170 is disposed in a body lumen 165. Stated another way, the deployment actuator 140 may be transitioned from a second position 142 (see FIGS. 6A and 6B) to a first position 141

(see FIG. 6C). Actuation of the deployment actuator 140 from the second position 142 to the first position 141 extends the delivery sheath 110 over the packaged and/or undeployed filter 170. Sheathing of the filter 170 may facilitate introduction of the filter 170 into the body lumen 165 and delivery of the sheathed filter 170 to a location within the body lumen 165. During an exemplary procedure, as shown in FIG. 6C, the coupled filter 170 may be sheathed prior to introduction into a body lumen 165.

Figure 6D:
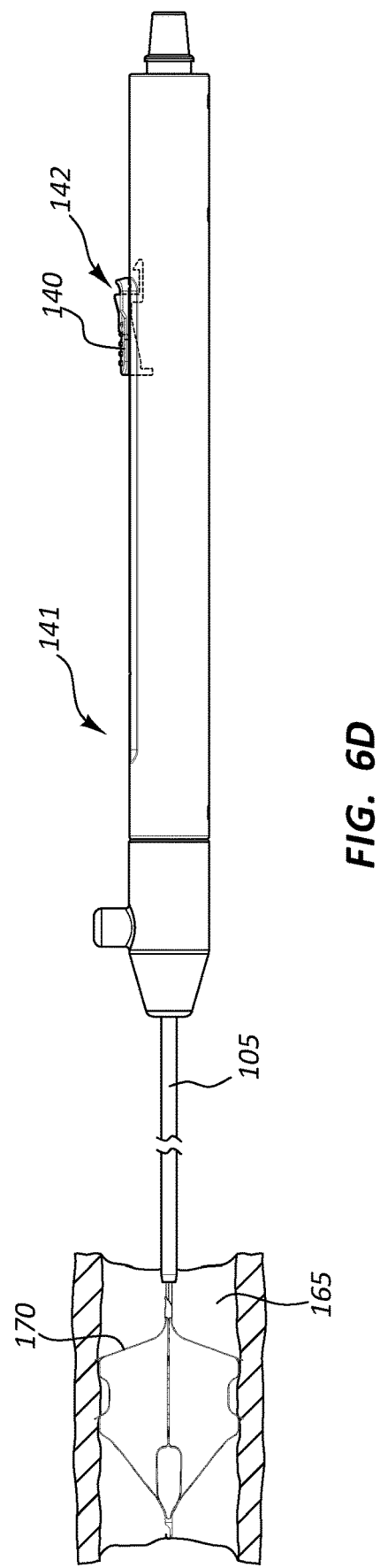
FIG. 6D is a side view of a filter deployment device assembly in a fourth configuration.

FIG. 6D is a side view of the filter deployment device assembly in a fourth configuration. As illustrated, the deployment actuator 140 has been transitioned from the first position 141 to the second position 142 such that the delivery sheath axially retracts within at least a portion of the introducer sheath 105 such that the filter 170 may deploy within the body lumen 165. Stated another way, actuating the deployment actuator 140 may retract the delivery sheath to deploy the filter 170. In an exemplary procedure, as illustrated in FIG. 6D, the delivery sheath (110 of FIG. 6C) may be retracted to deploy the filter 170 within the body lumen 165.

Figure 6E:
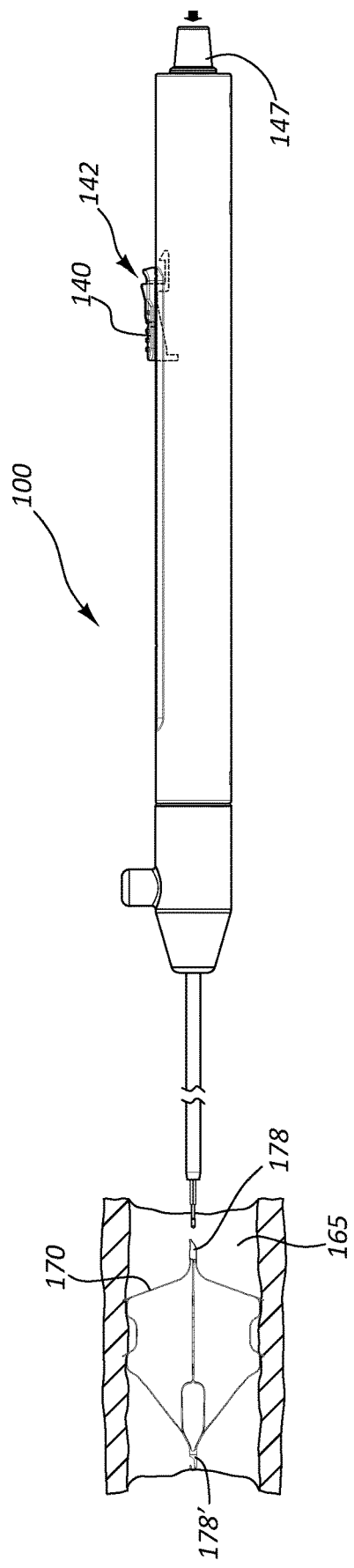
FIG. 6E is a side view of a filter deployment device assembly in a fifth configuration.

FIG. 6E is a side view of the filter deployment device assembly in a fifth configuration. In the illustrated embodiment, the coupling actuator 147 is actuated, as indicated by the arrow. Actuating the coupling actuator 147, when the deployment actuator 140 is in the second position 142, may distally displace the enlarged distal end 131 of the inner member 130 (FIG. 6B1) such that the filter 170 may be decoupled from the filter deployment device 100. In some embodiments, distally displacing the inner member of the filter coupling mechanism relative to the collet may be configured to decouple and/or release the filter 170. When the filter coupling mechanism is in the decoupling configuration, proximal displacement of the filter deployment device 100 may move the filter coupling mechanism away from the filter 170 as the interaction between the filter 170 and the body lumen 165 tends to maintain the position of the filter 170 as the filter deployment device 100 is withdrawn.

In the illustrated embodiment, the filter 170 comprises a first tube portion 178 adjacent a first end of the filter 170 and a second tube portion 178' adjacent a second end of the filter 170, such that the filter deployment device 100 may be coupled to either the first end or the second end of the filter 170. This flexibility may allow a user to insert the filter 170 into a body lumen 165 in a particular orientation when the filter 170 is introduced into the body lumen 165 from a variety of insertion points. For example, for disposition of the filter 170 in the inferior vena cava, a first filter orientation may be desirable for femoral insertion of the filter 170, and a second filter orientation may be desirable for jugular insertion of the filter 170. As depicted in FIG. 6E, during an exemplary procedure the filter 170 may be decoupled from the filter deployment device 100 and disposed within the body lumen 165.

In another embodiment, a method of deploying a filter is disclosed (see FIGS. 6A-6E), comprising coupling a filter 170 to a filter deployment device 100, introducing the filter 170 into a body lumen 165, deploying the filter 170, and decoupling the filter 170 from the filter deployment device 100, such that decoupling the filter 170 is independent of deploying the filter 170. In yet another embodiment, the method may comprise at least distally or proximally displacing the coupled filter 170 within the body lumen 165. A user may desire to distally and/or proximally displace the filter 170 so that the filter 170 may be properly positioned within the body lumen 165. In another embodiment, the decoupled filter 170 may be recoupled to the filter deployment device 100 either for repositioning of the filter 170 or for removal of the filter 170 from the body lumen 165. In embodiments, upon repositioning of the filter 170, the filter 170 may be decoupled from the filter deployment device 100.

FIGS. 7A and 7B illustrate a locking or safety mechanism, such as a release safety, configured to control, limit, and/or restrict inadvertent decoupling of a filter from a filter deployment device 100. A filter deployment device 100 may be configured to limit inadvertent decoupling of a filter. In a first configuration 141, decoupling of the filter may be controlled, limited, and/or restricted. In a second configuration 142, decoupling of the filter may be allowed and/or permitted. Referring to FIG. 7B, the locking safety mechanism comprises a delivery sheath 110 and a deployment member wherein the deployment member may be axially displaceable within the delivery sheath 110. The locking safety mechanism further comprises a filter coupling mechanism disposed adjacent a distal end of the deployment member, for example as discussed in connection with FIGS. 1-5A. The filter coupling mechanism may be configured to releasably couple a filter to the deployment member independent of the delivery sheath 110. As illustrated, the locking safety mechanism further comprises a coupling actuator 147 operatively coupled to the filter coupling mechanism via the deployment member 115. The coupling actuator 147 may be configured to decouple a filter with respect to the delivery sheath 110. The locking safety mechanism may further comprise a release safety that permits decoupling of the filter only when the filter is in a deployed configuration. For example, the coupling actuator 147 may be configured such that actuation of the coupling actuator 147 is configured to decouple a filter only when the filter is in a deployed and/or expanded configuration with respect to the delivery sheath 110.

The locking mechanism further comprises a deployment actuator 140 operatively coupled to the delivery sheath 110. Referring to FIGS. 7A and 7B, the deployment actuator 140 is displaceable between at least a first position 141 and a second position 142 such that displacement of the deployment actuator 140 from the first position 141 to the second position 142 may be configured to unsheathe a filter and allow and/or permit the filter to deploy and/or expand. The deployment actuator 140 may be configured to proximally displace the delivery sheath 110 with respect to a filter. As illustrated, the deployment actuator 140 comprises a notch engagement member 143 which may be configured to engage a locking notch 101 disposed on an inside surface of the filter deployment device 100. Engagement between the notch 101 and the notch engagement member 143 may be configured to lock and/or secure the deployment actuator 140 in the second position 142. In embodiments, a similar notch may be present to lock and/or secure the deployment actuator 140 in the first position 141.

As described above, and as illustrated in FIGS. 3-5, the coupling member of the locking mechanism may comprise an outer member 125 operatively coupled to both the deployment actuator 140 and the coupling actuator 147. The coupling member may further comprise an inner member 130, wherein the inner member 130 may be axially displaceable within the outer member 125. As illustrated in FIGS. 7A and 7B, the inner member 130 is operatively coupled to the coupling actuator 147, such that actuation of the coupling actuator 147 may simultaneously displace both the outer member 125 and the inner member 130 with respect to the delivery sheath 110 when the deployment actuator 140 is disposed in the first position 141. This displacement may be substantially simultaneous. As detailed above in FIG. 6A1, simultaneous displacement of the inner member 130 and the outer member 125 may not transition the coupling mechanism from a coupling configuration to a decoupling configuration. (Because relative displacement of the inner member with respect to the outer member is configured to transition the coupling mechanism to the decoupling configuration.) Thus, when the deployment actuator 140 is in the first position 141, actuation of the coupling actuator 147 may not decouple the filter 170, thus preventing decoupling when the deployment actuator 140 is in the first position 141, as further detailed below.

As also detailed below, the inner member 130 may be configured to be distally displaced with respect to the outer member 125 when the deployment actuator 140 is disposed, locked, and/or secured in the second position 142 and the coupling actuator 147 is actuated. The coupling actuator 147 may be actuated by a user, for example. In some embodiments, the deployment actuator 140 may be displaced between at least the first position 141 and the second position 142, or vice versa, by a user.

Also, as described above, and referring to FIGS. 3-5A, 7A, and 7B, the outer member 125 may comprise a collet 135 at or adjacent a distal end of the outer member 125. Further, the collet 135 may comprise a plurality of flexible legs 136. The inner member 130 may comprise an enlarged distal end 131. The enlarged distal end 131 may be configured to engage the collet 135 and bias radially outward the legs 136 of the collet 135. This configuration may result in coupling of a filter 170 to the outer member 125. In embodiments, disengagement of the distal portion of the inner member 130 may be configured to permit radial inward biasing and/or displacement of the legs 136 of the collet 135. This configuration may result in decoupling of the filter 170 from the outer member 125. In other embodiments, the inner member 130 may comprise an annular taper 133, as described above. In another embodiment, the collet 135 may be configured to releasably couple the outer member 125 to a tube portion 178 of a filter.

Referring again to FIGS. 7A and 7B, the locking mechanism may further comprise a first biasing member 150 operatively disposed between the coupling actuator 147 and a biasing member perch 158. As illustrated, a second biasing member 151 is operatively disposed between the biasing member perch 158 and a distal portion of a biasing member perch stop 159. In some embodiments, the biasing member perch 158 is displaceable with respect to the biasing member perch stop 159 when the deployment actuator 140 is in the first position 141 and the biasing member perch 158 may be fixed with respect to the biasing member perch stop 159 when the deployment actuator 140 is in the second position 142, as detailed below.

As illustrated in FIGS. 7A and 7B, the deployment actuator 140 may be further coupled to a sheath body 155 comprising a cap 156 and a cap extension 157 and a biasing member perch 158 may be operably coupled to the second biasing member 151. When the deployment actuator 140 is disposed, locked, and/or secured in the second position 142, the cap extension 157 abuts the biasing member perch 158, engaging and/or pressing the biasing member perch 158 against a proximal portion of the biasing member perch stop 159. The described configuration controls, minimizes, and/or resists compression of the second biasing member 151 upon actuation of the coupling actuator 147 while compression of the first biasing member 150 is allowed and/or permitted. As illustrated in FIG. 7A, when the deployment actuator 140 is disposed in the first position 141, the cap extension 157 does not abut the biasing member perch 158 and thus the biasing member perch 158 may not engage and/or press against the biasing member perch stop 159. The described configuration of FIG. 7A allows and/or permits compression of both the first biasing member 150 and the second biasing member 151 upon actuation of the coupling actuator 147.

In embodiments, the first biasing member 150 may exert a greater biasing force than the second biasing member 151. A first biasing force exerted by the first biasing member 150 may displace the biasing member perch 158 when the coupling actuator 147 is displaced and the deployment actuator 140 is in the first position 141. A second biasing force exerted by the second biasing member 151 may resist displacement of the biasing member perch 158 when the coupling actuator 147 is displaced and the deployment actuator 140 is in the first position 141. In other embodiments, the first biasing member 150 may comprise a first spring or other biasing mechanism, and the second biasing member 151 may comprise a second spring or other biasing mechanism. It is also within the scope of this disclosure for a safety mechanism, such as that described above, to be actuated independently of a mechanism configured to control sheathing of a filter.

A method of avoiding inadvertent decoupling of a filter from a filter deployment device is also disclosed, comprising coupling a filter 170 to the filter coupling mechanism, actuating the deployment actuator 140 to extend the delivery sheath 110 over the filter 170, introducing the sheathed filter into a body lumen 165, actuating the deployment actuator 140 to retract the delivery sheath 110 to deploy the filter 170, and decoupling the filter 170 from the filter deployment device 100 by actuating a coupling mechanism or a coupling actuator 147, wherein actuation of the coupling mechanism or the coupling actuator 147 is configured to decouple the filter 170 only when the filter 170 is deployed from the delivery sheath 110.

FIG. 8 is a perspective view of another embodiment of a filter deployment device 200 coupled to a filter packaging cartridge 290, comprising another embodiment of a locking or safety mechanism. The indicia on the illustrated filter packaging cartridge 290 are for example only and other indicia are contemplated. As illustrated, the filter packaging cartridge 290 is coupled to the filter deployment device 200 at or adjacent a distal end of a handle portion of the filter deployment device 200. The embodiment of FIG. 8 may include components that resemble components of the embodiment of FIG. 1 in some respects. For example, the embodiment of FIG. 8 includes an introducer sheath 205 that may resemble the introducer sheath 105 of FIG. 1. It will be appreciated that all the illustrated embodiments have analogous features. Accordingly, like features are designed with like reference numerals, with leading digits added to increment each reference numeral by 100. (For instance, the introducer sheath is designated "105" in FIG. 1 and analogous introducer sheath is designated as "205" in FIG. 8.) Relevant disclosure set forth above regarding similarly identified features thus may not be repeated hereafter. Moreover, specific features of the filter deployment device and related components shown in FIG. 8 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the filter deployment device and related components of FIG. 8. Any suitable combination of the features, and variations of the same, described with respect to the filter deployment device and components illustrated in FIG. 1 can be employed with the filter deployment device and components of FIG. 8, and vice versa. This pattern of disclosure applies equally to further embodiments depicted in subsequent figures and/or described hereafter.

FIGS. 9A-9F depict several configurations of the locking or safety mechanism of the embodiment of FIG. 8. The locking or safety mechanism may comprise a release safety, configured to control, limit, and/or restrict inadvertent decoupling of a filter 270 from a filter deployment device 200. It will be appreciated by one skilled in the art having the benefit of this disclosure that the filter deployment device described herein may be used in connection with other filters or devices in addition to the exemplary filter illustrated in this or any other figure. A filter deployment device 200 may be configured to limit inadvertent decoupling of the filter 270. The embodiment of FIGS. 9A-9F may utilize a filter packaging cartridge as an element of a locking or safety mechanism. For example, referring to FIG. 9A, the locking safety mechanism comprises a filter packaging cartridge 290, an introducer sheath 205 coupled to a hub 206, and a deployment member 215 wherein the deployment member 215 may be axially displaceable within both of the filter packaging cartridge 290 and the introducer sheath 205. Decoupling of the filter 270 may be controlled, limited, and/or restricted depending on the relative position of the filter packaging cartridge 290 with respect to other components.

The filter deployment device 200 may comprise a filter coupling mechanism disposed adjacent a distal end of the deployment member 215. For example, in some embodiments, a coupling mechanism such as that discussed in connection with FIGS. 1-5A may be utilized with the filter deployment device 200 of FIGS. 9A-9F. The filter coupling mechanism may be configured to releasably couple the filter 270 to the deployment member 215 independent of the introducer sheath 205. As illustrated, the locking safety mechanism of the filter deployment device 200 further comprises a first coupling actuator 247a and a second coupling actuator 247b operatively coupled to the filter coupling mechanism via the deployment member 215. The first and/or second coupling actuators 247a, 247b may be configured to decouple the filter 270 with respect to the introducer sheath 205. The locking safety mechanism may further comprise a release safety that permits decoupling of the filter 270 only when the filter 270 is in a deployed configuration. For example, the first and/or second coupling actuators 247a, 247b may be configured such that actuation of the first and/or second coupling actuators 247a, 247b is configured to decouple a filter 270 only when the filter 270 is in a deployed and/or expanded configuration with respect to the introducer sheath 205.

Figure 9A:
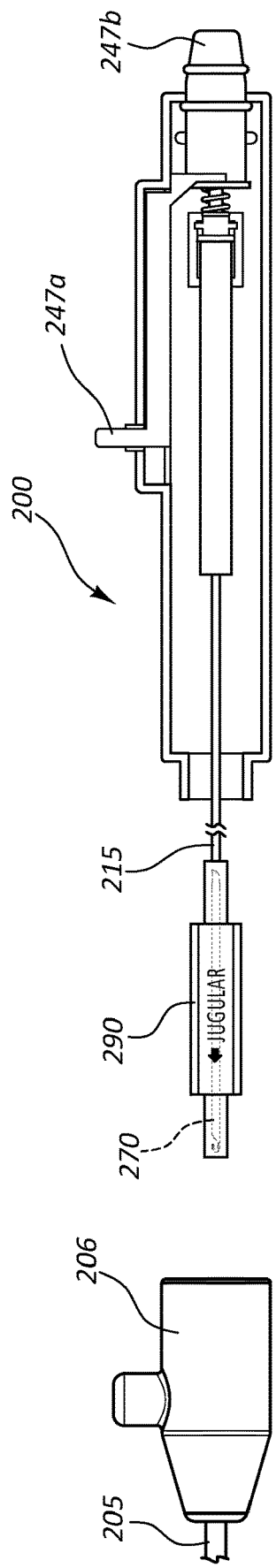
FIG. 9A is a partial cross-sectional side view of the filter deployment device of FIG. 8 depicting another embodiment of a locking or safety mechanism in a first configuration.
Figure 9B:
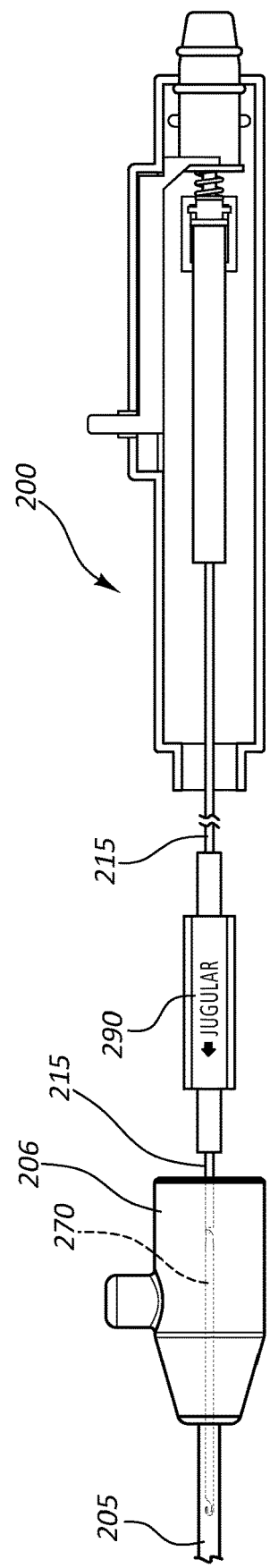
FIG. 9B is a partial cross-sectional side view of the filter deployment device of FIG. 8 depicting the locking or safety mechanism in a second configuration.

The locking safety mechanism may further comprise a hub 206 operatively coupled to the introducer sheath 205. In the configuration of FIG. 9B, the filter 270 is coupled to the deployment member 215, such that the filter 270 may be extended into and/or through the hub 206 and into and/or through the introducer sheath 205. Further, as illustrated, the filter packaging cartridge 290 remains axially displaceable along the deployment member 215 upon displacement of the filter 270 into and/or through the hub 206 and/or introducer sheath 205.

Figure 9C:
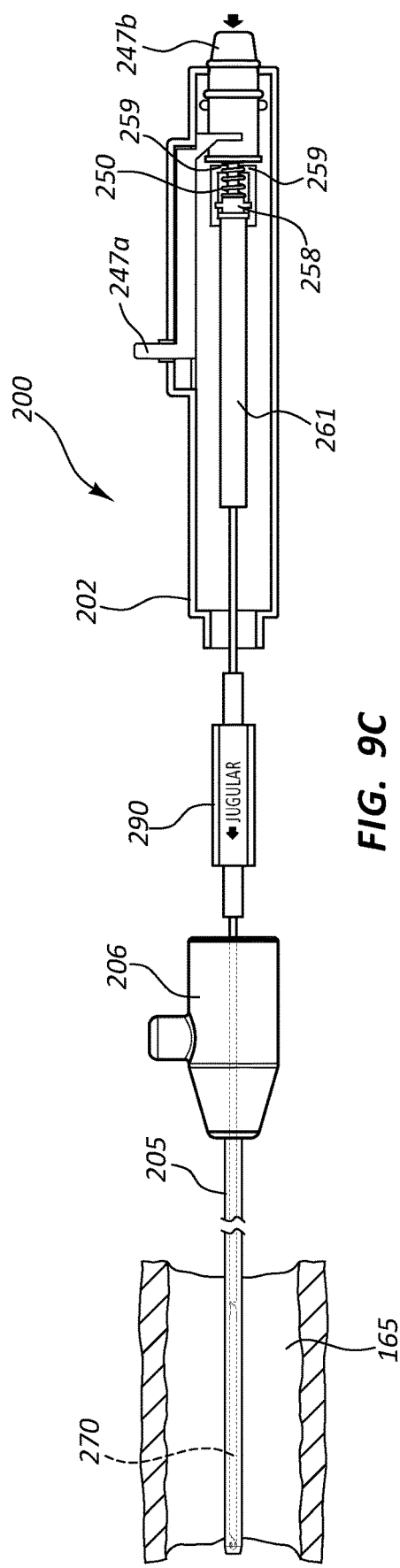
FIG. 9C is a partial cross-sectional side view of the filter deployment device of FIG. 8 depicting the locking or safety mechanism in a third configuration.
Figure 9D:
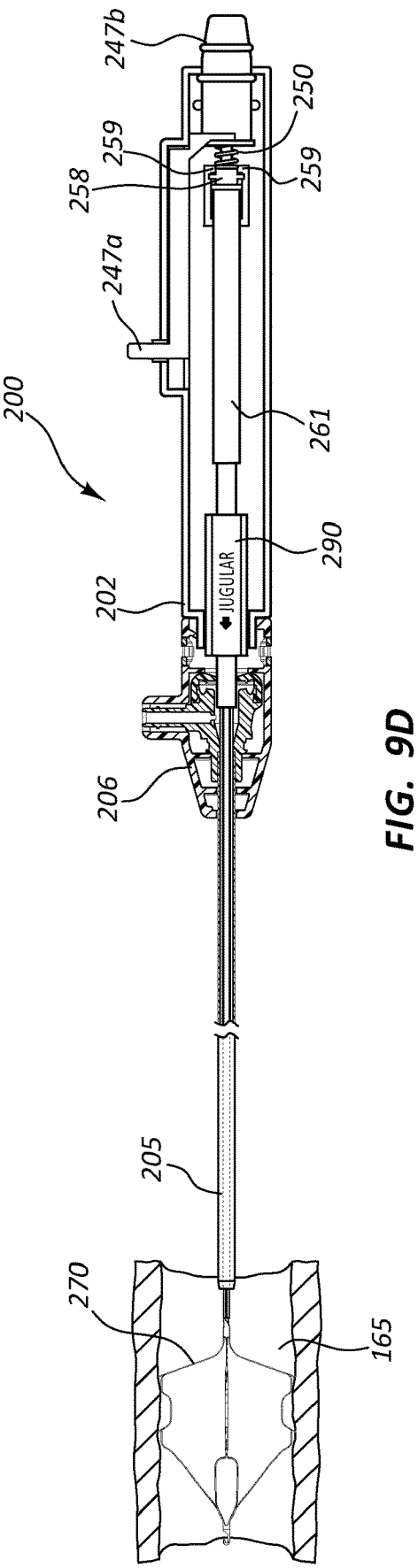
FIG. 9D is a partial cross-sectional side view of the filter deployment device of FIG. 8 depicting the locking or safety mechanism in a fourth configuration.

FIGS. 9C-9F depict introduction, deployment, decoupling, and disposition of the filter 270 in a body lumen 165. Referring to FIGS. 9C and 9D, the hub 206 is displaceable with respect to a filter deployment device handle 202, the deployment member, and the filter 270 between at least an unengaged position (as in FIG. 9C) and an engaged position (as in FIG. 9D). The sheath 205 may be coupled to the hub 206 such that displacement of the hub 206 with respect to the deployment member from the unengaged position to the engaged position may be configured to unsheathe the filter 270 and allow and/or permit the filter 270 to deploy and/or expand. Thus, the hub 206 may be configured to proximally displace the introducer sheath 205 with respect to the filter 270. In some embodiments, the hub 206 may comprise a first engagement member which may be configured to engage a second engagement member disposed at a distal end of the filter deployment device handle 202. Engagement between the first engagement member and the second engagement member may be configured to lock and/or secure the hub 206 in the engaged position, and subsequently, deployment of the filter may be allowed and/or permitted, as further detailed below.

Again, the filter deployment device 200 of FIGS. 9A-9F may comprise a coupling mechanism such as that described in connection with FIGS. 3-5. Specifically, the filter deployment device 200 may comprise elongate components configured to transition the filter deployment device 200 between a filter coupling configuration and a filter decoupling configuration when the elongate components are axially displaced relative to each other. For example, the filter deployment device 200 may comprise an outer member (such as outer member 125 of FIG. 3) and an inner member (such as inner member 130 of FIG. 3). As with the embodiment of FIGS. 3-5, relative displacement of the outer and inner members with respect to each other may be configured to couple and/or decouple the filter 270 from the filter deployment device 200.

Still further, the outer and inner members of the filter deployment device 200 may comprise analogous components to the outer and inner members of the embodiment of FIGS. 3-5A. Specifically, as with the embodiment of FIGS. 3-5A, the outer member may comprise a collet (such as collet 135 of FIG. 3 at or adjacent a distal end of the outer member). Further, the collet may comprise a plurality of flexible legs (such as flexible legs 136 of FIG. 3). The inner member may comprise an enlarged distal end (such as enlarged distal end 131 of FIG. 3). The enlarged distal end may be configured to engage the collet and bias radially outward the legs of the collet. This configuration may result in coupling of a filter 270 to the outer member. Further, disengagement of the distal portion of the inner member may be configured to permit radial inward biasing and/or displacement of the legs of the collet. This configuration may result in decoupling of the filter 270 from the outer member.

As illustrated in FIGS. 9C and 9D, the coupling member of the locking mechanism may comprise a first biasing member 250 and at least one of the first and second coupling actuators 247a, 247b. The first biasing member 250 and one or both of the first and second coupling actuators 247a, 247b may be operatively coupled to the outer and inner members of filter deployment device 200. For example, in the embodiment of FIGS. 9C and 9D, the inner member is operatively coupled to at least one of the first and second coupling actuators 247a, 247b, and the outer member is operatively coupled to the first biasing member 250. When the first biasing member 250 is unconstrained, actuation of the first or second coupling actuators 247a, 247b displaces both the actuated coupling actuator 247a, 247b and the first biasing member 250. Thus, actuation of the at least one coupling actuator 247a, 247b (without constraining the first biasing member 250) may simultaneously displace both the outer member and the inner member with respect to the introducer sheath 205. (The configuration in which the first biasing member is unconstrained correlates to the configuration wherein the hub 206 is disposed in the unengaged position in the illustrated embodiment.) This displacement may be substantially simultaneous. Analogous to the embodiment described in connection with FIG. 6A1, above, simultaneous displacement of the inner member and outer member may not transition the coupling mechanism from a coupling configuration to a decoupling configuration. (Because relative displacement of the inner member with respect to the outer member is configured to transition the coupling mechanism to the decoupling configuration.) Thus, when the hub 206, referring again to FIGS. 9C and 9D, is in the unengaged position, actuation of the at least one coupling actuator 247a, 247b may not decouple the filter 270, thus preventing decoupling when the hub 206 is in the unengaged position, as further detailed below.

The inner member may be configured to be distally displaced with respect to the outer member, thus transitioning the filter deployment device 200 from a filter coupling configuration to a filter decoupling configuration, when the first biasing member 250 is constrained and the at least one coupling actuator 247a, 247b is actuated. As detailed below, disposition of the hub 206 in the engaged position is configured to constrain the filter packaging cartridge 290 which in turn, constrains the first biasing member 250 in the illustrated embodiment. Again, thus constraining the first biasing member 250 correlates to configuring the filter deployment device 200 such that actuation of the first or second coupling actuator 247a, 247b will decouple a filter from the filter deployment device 200. The at least one coupling actuator 247a, 247b may be actuated by a user, for example. In some embodiments, the hub 206 may be displaced between at least the unengaged position and the engaged position, or vice versa, by a user.

Referring again to FIGS. 9C and 9D, the first biasing member 250 may be disposed such that a distal end of the first biasing member 250 is operatively coupled to a biasing member perch 258. The first biasing member 250 may be operatively disposed between at least one of the first and second coupling actuators 247a, 247b and a proximal end of a perch engagement tube 261. As illustrated, the perch engagement tube 261 is operatively disposed between the biasing member perch 258 and a proximal end of the filter packaging cartridge 290. In some embodiments, the biasing member perch 258 is displaceable with respect to a biasing member perch stop 259 when the hub is in the unengaged position and the biasing member perch 258 may be fixed with respect to the biasing member perch stop 259 when the hub 206 is in the engaged position, as detailed below.

As illustrated in FIG. 9C, when the hub 206 is disposed in the unengaged position, the proximal end of the perch engagement tube 261 does not press and/or secure the biasing member perch 258 against the biasing member perch stop 259. The described configuration of FIG. 9C controls and/or limits compression of the first biasing member 250 upon actuation of the first and/or second coupling actuators 247a, 247b. Stated another way, when the hub 206 is in the disengaged position the biasing member perch 258 may move upon actuation of the first and/or second coupling actuators 247a, 247b, thus the first biasing member 250 may not be compressed upon actuation of the first and/or second coupling actuators 247a, 247b, so the filter 270 cannot be released. As illustrated in FIGS. 9D and 9E, when the hub 206 is disposed, locked, and/or secured in the engaged position, the proximal end of the perch engagement tube 261 abuts the biasing member perch 258, engaging and/or pressing the biasing member perch 258 against a proximal portion of the biasing member perch stop 259, so the filter 270 can be released. In the described configuration, compression of the first biasing member 250 is allowed and/or permitted. Thus, as shown in FIG. 9E, actuation of at least one of the first and/or second coupling actuators 247a, 247b, when the hub 206 is in the engaged position, can result in decoupling of the filter 270 from the deployment member 215. Upon decoupling of the filter 270, as shown in FIG. 9F, the introducer sheath 205 may be removed from the body lumen 165 by proximally displacing the filter deployment device 200 as indicated by the arrows, such that the filter 270 remains positioned at a desired location with the body lumen 165.

In some embodiments, the first biasing member 250 may comprise a first spring or other biasing mechanism. It is also within the scope of this disclosure for a safety mechanism, such as that described above, to be actuated independently of a mechanism configured to control sheathing of a filter.

FIG. 10A is a partial cross-sectional side view of a portion of the filter deployment device 200 of FIG. 8, in the configuration of FIG. 9F. First coupling actuator 247a is operatively coupled to second coupling actuator 247b. As illustrated, neither the first coupling actuator 247a nor the second coupling actuator 247b is in an actuated configuration. FIG. 10B is a partial cross-sectional side view of a portion of the filter deployment device 200 of FIG. 8, in the configuration of FIG. 9E. As illustrated, the first coupling actuator 247a is in an actuated configuration. As indicated by the arrows, actuation of the first coupling actuator 247a by a radially inward force is translated into a horizontal force such that the second coupling actuator 247b and its associated components are distally displaced. Specifically, cam surface 248 of the first coupling actuator 247a engages and interacts with a flange 249 of the second coupling actuator 247b, resulting in distal displacement of the second coupling actuator 247b, and its associated components, upon actuation of the first coupling actuator 247a. In other words, actuation of either the first coupling actuator 247a or the second coupling actuator 247b may result in distal displacement of at least the deployment member 215.

Another method of avoiding inadvertent decoupling of a filter from a filter deployment device is also disclosed (FIGS. 9A-9F), comprising introducing a sheathed filter into a body lumen 165, displacing the hub 206 to retract the introducer sheath 205 to deploy the filter 270, and decoupling the filter 270 from the filter deployment device 200 by actuating a coupling mechanism or at least one of a first and/or second coupling actuators 247a, 247b, wherein actuation of the coupling mechanism or the at least one coupling actuator 247a, 247b is configured to decouple the filter 270 only when the filter 270 is deployed from the introducer sheath 205.

FIGS. 11A-11C depict various configurations of a filter packaging cartridge 190. In the illustrated embodiment, the filter packaging cartridge 190 comprises an elongate member 192, and the elongate member 192 is configured to retain at least a portion of the filter 170. In some embodiments, the elongate member 192 may only partially surround the filter 170. In the illustrated embodiment, the filter packaging cartridge 190 further comprises a toggling member, such as tab 194, operatively coupled to the elongate member 192. The tab 194 may be configured to toggle, move, and/or transition the elongate member 192 between at least a first configuration as illustrated in FIG. 11B and a second configuration as illustrated in FIG. 11C. As illustrated, the first configuration exposes a first end portion of the filter 170, and the second configuration exposes a second end portion of the filter 170. In embodiments, the exposed end portion of the filter 170 is available for coupling to a filter deployment device 100 (FIG. 1).

In some embodiments, the tab 194 may comprise indicia such as labels. In other embodiments, the indicia may be configured to indicate to a user or users how to selectively orient a filter 170 for coupling the filter 170 to the filter deployment device. In yet other embodiments, the indicia may indicate to the user how to selectively couple the filter 170 to the filter deployment device for jugular insertion of the filter 170 into a body lumen. In still other embodiments, the indicia may indicate to the user how to selectively couple the filter 170 to the filter deployment device for femoral insertion of the filter 170 into a body lumen. As illustrated in FIGS. 11B and 11C, respectively, the first indicia are only visible when the first end of the filter 170 is exposed, and the second indicia are only visible when the second end of the filter 170 is exposed. The upstream or downstream orientation of the filter 170, when disposed within a body lumen, such as the inferior vena cava, may not be the same if the filter 170 were coupled at the same end of the filter 170 and inserted into a body lumen femorally or jugularly. Selective coupling of the filter 170 to the filter deployment device may properly orient the filter 170 for disposition within a body lumen depending on the insertion point of the filter 170.

In another embodiment, the tab 194 may be configured to orient a filter 170 with respect to a filter deployment device to control which end of the filter 170 is positioned downstream when deployed in a body lumen. The filter packaging cartridge 190 may be further configured to be compatible with a variety of other filters and devices.

In another embodiment, the present disclosure may comprise a filter packaging cartridge kit. The kit may comprise a filter 170, an elongate member 192 configured to at least partially retain the filter 170, and a tab 194 operatively coupled to the elongate member 192 (FIGS. 11A-11C). As described above, the tab 194 may be configured to toggle, move, and/or transition the elongate member 192 between at least a first configuration and a second configuration. The first configuration may expose a first end portion of the filter 170 (FIG. 11B), and the second configuration may expose a second end portion of the filter 170 (FIG. 11C). The exposed end portion may be available for coupling the filter 170 to the filter deployment device.

In embodiments, the filter packaging cartridge kit may comprise a filter packaging cartridge 190 wherein at least one of the tab 194 and/or the filter 170 comprises indicia, such as labels. In one embodiment, as illustrated in FIGS. 11B and 11C, the filter 170 may comprise indicia of the orientation of the filter 170 within the elongate member 192. In embodiments, the indicia may be disposed adjacent at least one of a first end portion and/or a second end portion of the filter 170. The indicia as depicted in FIGS. 11B and 11C are for illustrative purposes only, and other indicia configurations, contents, systems, and types are contemplated. As illustrated in FIG. 11B, the indicia may be positioned at or adjacent a first end portion of the filter 170. As illustrated in FIG. 11C, the indicia may be positioned at or adjacent a second end portion of the filter 170. The indicia of the tab 194 in the kit may be similar to those described above for the filter packaging cartridge 190.

As described above, the indicia on the filter 170 may be configured to indicate to a user or users how to selectively orient the filter 170 for coupling of the filter 170 to a filter deployment device. In embodiments, a first indicia may indicate to a user how to selectively couple the filter 170 to a filter deployment device for jugular insertion of the filter 170. As illustrated in the embodiment of FIG. 11B, the first indicia are only visible when the first end of the filter 170 is exposed. A second indicia may indicate to a user how to selectively couple the filter 170 to a filter deployment device for femoral insertion of the filter 170. As illustrated in the embodiment of FIG. 11C, the second indicia are only visible when the second end of the filter 170 is exposed. In some embodiments, the tab 194 may be configured to orient the filter 170 of the kit with respect to a filter deployment device to control which end of the filter 170 is positioned downstream when deployed in a body lumen.

A method of coupling a vascular filter to a deployment device is disclosed which may comprise obtaining a vascular filter disposed within a filter packaging cartridge 190, and selectively toggling, moving, and/or transitioning the elongate member 192 of the filter packaging cartridge 190 between at least a first configuration (FIG. 11B) and a second configuration (FIG. 11C). The first configuration may expose a first end portion of a filter 170, and the second configuration may expose a second end portion of the filter 170. In embodiments, the exposed end portion of the filter 170 may be available for coupling to a filter deployment device. The method may further comprise coupling the exposed end portion of the filter 170 to the filter deployment device.

As disclosed above for the filter packaging cartridge 190 and/or the filter packaging cartridge kit, at least one of the tab 194 and/or the filter 170 may comprise indicia. In embodiments, the indicia may be configured to indicate to a user how to selectively orient the filter 170 for coupling the filter 170 to a filter deployment device. In another embodiment, the method may further comprise selectively coupling the filter 170 to the filter deployment device 100 for jugular insertion of the filter 170. In other embodiments, the method may further comprise selectively coupling the filter 170 to the filter deployment device 100 for femoral insertion of the filter 170. In yet other embodiments, the method may further comprise selectively coupling the filter 170 to the filter deployment device 100 for downstream disposition of the filter 170 in a body lumen.

In another embodiment (see FIGS. 11A-11C), a method of using a filter packaging cartridge 190 may comprise grasping a filter packaging cartridge 190 retaining a body lumen filter 170, toggling the filter packaging cartridge 190 relative to the filter 170 such that one of a first or second end of the filter 170 is available for coupling to a filter deployment device, and coupling the available end of the filter 170 to the filter deployment device. The step of toggling the filter packaging cartridge 190 may further comprise displacing the filter packaging cartridge 190 between at least a first position and a second position such that one of the first end or the second end of the filter 170 is exposed. The step of coupling the filter 170 may further comprise using indicia of the filter packaging cartridge 190 to selectively orient the filter 170 for coupling to a filter deployment device, using indicia on the filter 170 to selectively orient the filter 170 for coupling to a filter deployment device, selectively coupling the filter 170 to the filter deployment device for jugular insertion of the filter 170, selectively coupling the filter deployment device for femoral insertion of the filter 170, and/or selectively coupling the filter 170 to the filter deployment device for downstream disposition of the filter 170 in a body lumen.

Other suitable methods of using a filter packaging cartridge 190 are also within the scope of this disclosure.

FIG. 12A depicts a filter 170 for a body lumen. As illustrated, the filter 170 comprises a first axial portion 175 at or adjacent a first end of the filter 170, a second axial portion 176 at or adjacent a second end of the filter 170, and a plurality of extensions 180 disposed between and coupled to the first and second axial portions 175, 176. Each extension 180 comprises an outside surface 185 and an inside surface 186, wherein the inside surface 186 tapers to a point 187. FIG. 12B is a perspective cross-sectional view of the body lumen filter 170 of FIG. 12A taken through line 12B-12B. As illustrated, a cross section of at least a portion of each extension 180 is substantially trilateral or triangular. In embodiments, the entirety of each extension 180 comprises a trilateral or triangular cross section. In other embodiments, only a portion or portions of each extension 180 comprise a trilateral or triangular cross section. In some embodiments, at least two sides of the trilateral cross section may be arced or curved and taper to a point.

As illustrated in FIGS. 12A and 12B, at least a portion of the outside surface 185 of each extension 180 is configured to contact a surface of a body lumen. In embodiments, at least a portion of the inside surface 186 is configured to slice through at least a portion of tissue ingrowth or tissue encapsulation in a body lumen. For example, after placement of the filter 170 in a body lumen, tissue may grow around at least a portion of the filter 170 or tissue may encapsulate a portion of the filter 170 geometry. In another example, the tissue may grow around at least the portion or portions of the filter 170 that come into contact with the body lumen. This growth may be termed tissue ingrowth or tissue encapsulation; such ingrowth or encapsulation may make it difficult to move or adjust a position of a filter 170 in a body lumen or to remove the filter 170 from the body lumen. A filter 170 comprising extensions 180, wherein the extensions 180 comprise an inside surface 186 comprising a surface that tapers to a point 187, may be desirable for ease of filter 170 recoupling to and/or removal from a body lumen. In other embodiments, the inside surface 186 of the extensions 180 may be configured to ease retrieval of the filter 170 from a body lumen.

Filter 170 also includes a plurality of extensions 180, which, in the embodiment of FIGS. 12A and 12B, includes four extensions 180. In other embodiments, the plurality of extensions 180 may have more or fewer extensions, for example, from three to 12 extensions, from five to 10 extensions, or from six to nine extensions, or specifically three, five, six, seven, eight, nine, 10, 11, 12, or any other number of extensions. Likewise, while in the embodiment of FIGS. 12A and 12B each extension 180 of the plurality of extensions has substantially the same shape as the other extensions 180, in other embodiments, different extensions on the same filter may have different shapes. Further, though in the embodiment of FIG. 9 the extensions 180 are substantially evenly spaced circumferentially around the center axis of the filter 170, in other embodiments the extensions 180 may be irregularly spaced.

In some embodiments, the filter 170 may be comprised of a shape memory alloy, for example Nitinol. Thus, the filter 170 may be comprised of a material which is first "set" in a particular shape when the filter is being manufactured, then tends to return to that shape if it is subsequently deformed. The filter 170 may be "set" in the expanded configuration, or the shape generally shown in FIG. 12A. Drawing the filter 170 into a delivery sheath may thus temporarily compress the extensions 180 within the delivery sheath, though the filter 170 may be configured to return to the expanded shape upon deployment from the delivery sheath. Thus, a filter may be configured with radially expanding extensions which are elastically compressible into a position substantially parallel with the axis of the filter.

In embodiments, at least one extension 180 may further comprise a first peak 181a and a second peak 181b wherein the second peak 181b is disposed longitudinally from the first peak 181a. The at least one extension 180 may further comprise a valley 182, wherein the valley extends longitudinally between the first and second peaks 181a, 181b. The at least one extension 180 may further comprise a leg 183, or a plurality of legs 183, wherein the legs 183 are disposed between the first peak 181a and a body member 188. In other embodiments, the legs 183 may extend radially outward from the body member 188 when the filter 170 is deployed.

In yet other embodiments, the at least one extension 180 may comprise a plurality of barbs 184, and the plurality of barbs 184 may be formed from center portions of the at least one extension 180. Furthermore, one or more barbs 184 may be configured to align with a portion of the extension 180 to which the barb 184 is coupled when the extensions 180 are drawn into a delivery sheath.

In some embodiments, the filter 170 may be integrally formed from the material of the tube portions 178, 178'. In other embodiments, the filter 170 and the tube portions 178, 178' may be formed from different materials.

In another embodiment, the filter for a body lumen may comprise a body member 188, and a plurality of extensions 180 coupled to and projecting from the body member 188. In some embodiments, at least one of the extensions 180 may comprise a substantially flat and/or planar outside surface 185, and/or an inside surface 186 wherein the inside surface 186 tapers to a point 187. In embodiments, the point 187 may be sharp. A cross section of at least a portion of one of the extensions 180 may be substantially triangular or trilateral. In some embodiments, a cross section of portions of the extensions 180 that are configured to come into contact with a surface of a body lumen may be substantially triangular and/or trilateral. In embodiments, at least a portion of the outside surface 185 of at least one of the extensions 180 may be configured to contact a surface of the body lumen. In further embodiments, the inside surface 186 of at least one of the extensions 180 may be configured to slice through at least a portion of ingrown tissue or encapsulating tissue in a body lumen. In yet other embodiments, at least a portion of the inside surface 186 of at least one of the extensions 180 may be configured to ease retrieval of the filter 170 from the body lumen.

The triangular or trilateral cross section as described herein is compatible with a wide variety of vascular filters including, but not limited to, bird's nest filters, conical filters, tulip-shaped filters, filters comprising free ends extending therefrom, and other filters.

A method of retrieving a body lumen filter from a body lumen is also disclosed. With reference to FIG. 12A, the method may comprise coupling a filter 170 comprising a plurality of extensions 180 to a filter retrieval device, displacing the filter 170 proximally such that an inside surface 186 of the extensions 180 each comprise a taper to a point 187 that slices through ingrown tissue or encapsulating tissue, and removing the coupled filter 170 from the body lumen.

Exemplary Embodiments

The following embodiments are illustrative and exemplary and not meant as a limitation of the scope of the present disclosure in any way.

I. Filter Deployment Devices

In one embodiment, a filter deployment device comprises: (1) a delivery sheath; (2) a deployment member axially displaceable within the delivery sheath; and (3) a filter coupling mechanism disposed adjacent a distal end of the deployment member, the filter coupling mechanism configured to releasably couple a filter to the deployment member independent of the delivery sheath.

The deployment member and the filter coupling mechanism may be configured to proximally and distally displace a filter independent of the position of the filter with respect to the delivery sheath.

The deployment member and the filter coupling mechanism may be configured to proximally and distally displace the filter when the filter is disposed outside the delivery sheath.

The filter coupling mechanism may comprise: (1) an outer member configured to selectively engage a filter; and (2) an actuating member axially displaceable with respect to the outer member, wherein displacement of the actuating member with respect to the outer member is configured to selectively couple the filter to the outer member.

The actuating member may comprise an inner member axially displaceable within the outer member.

The outer member may comprise a collet adjacent a distal end of the outer member, the collet may be configured to releasably couple the filter to the outer member.

The collet may comprise a plurality of flexible legs.

The inner member may comprise: (1) a proximal section; (2) a middle section; and (3) a distal section configured to engage the collet, wherein an outside diameter of the distal section is greater than an outside diameter of the middle section.

Distal displacement of the distal section of the inner member with respect to the collet may be configured to decouple the filter from the outer member.

The inner member may further comprise an annular taper disposed between the distal section and the middle section, the annular taper may be configured to engage an inside surface of the collet such that a portion of the collet is biased radially outward when the collet is in a filter coupling configuration.

The annular taper may be further configured to disengage from the inside surface of the collet when the collet is in a filter decoupling configuration.

The collet may be configured to releasably couple the outer member to a tube portion of a filter.

The collet may be configured to be at least partially disposed within the tube portion.

An outside diameter of a portion of the collet disposed within the tube portion may be less than an inside diameter of the tube portion when the collet is in the filter decoupling configuration, and such that the outside diameter of the portion of the collet disposed within the tube portion is biased into contact with the inside diameter of the tube portion when the collet is in the filter coupling configuration, such that the collet is configured to couple the outer member to the filter when the collet is in the filter coupling configuration and the collet is configured to decouple the outer member from the filter when the collet is in the filter decoupling configuration.

The delivery sheath may be configured to retract to deploy a filter disposed within the delivery sheath.

The filter coupling mechanism may be further configured to recouple a decoupled filter.

The delivery sheath may be configured to extend to dispose the recoupled filter within the delivery sheath.

The filter deployment device may further comprise one or more radiopaque markers.

The radiopaque markers may comprise gold.

II. Filter Deployment Assemblies

In one embodiment, a filter deployment assembly may comprise: (1) a delivery sheath; (2) a filter axially displaceable within the delivery sheath; (3) a deployment member axially displaceable within the delivery sheath; and (4) a filter coupling mechanism disposed adjacent a distal end of the deployment member, the filter coupling mechanism configured to releasably couple the filter to the deployment member independent of the delivery sheath.

The deployment member and the filter coupling mechanism may be configured to proximally and distally displace the filter independent of the position of the filter with respect to the delivery sheath.

The deployment member and the filter coupling mechanism may be configured to proximally and distally displace the filter when the filter is disposed outside the delivery sheath.

The filter may comprise: (1) a first axial portion adjacent a first end of the filter; and (2) a second axial portion adjacent a second end of the filter, wherein the filter coupling mechanism is configured to releasably couple the deployment member to either one of the first axial portion or the second axial portion of the filter.

The filter coupling mechanism may comprise: (1) an outer member configured to selectively engage the filter; and (2) an inner member axially displaceable within the outer member, wherein displacement of the inner member with respect to the outer member is configured to selectively couple the filter to the outer member.

The outer member may comprise a collet adjacent a distal end of the outer member, and the collet may be configured to releasably couple the filter to the outer member.

The collet may comprise a plurality of flexible legs.

The inner member may comprise: (1) a proximal section; (2) a middle section; and (3) a distal section configured to engage the collet, wherein an outside diameter of the distal section is greater than an outside diameter of the middle section.

Distal displacement of the distal section of the inner member with respect to the collet may be configured to decouple the filter from the outer member.

The inner member may further comprise an annular taper disposed between the distal section and the middle section, the annular taper configured to engage an inside surface of the collet such that a portion of the collet is biased radially outward when the collet is in a filter coupling configuration.

The annular taper may be further configured to disengage from the inside surface of the collet when the collet is in a filter decoupling configuration.

The first axial portion of the filter may comprise a first tube portion, and the second axial portion of the filter may comprise a second tube portion.

The first axial portion of the filter may comprise a first hook, and the second axial portion of the filter may comprise a second hook.

The collet may be configured to couple the outer member to the first or second tube portion.

The collet may be configured to be at least partially disposed within either the first or second tube portion.

An inside diameter of the tube portion of the first axial portion and the second axial portion may be greater than an outside diameter of a portion of the collet disposed within the tube portion when in the filter decoupling configuration, and an inside diameter of the tube portion of the first axial portion and the second axial portion of the filter may be biased into contact with the outside diameter of the portion of the collet disposed within the tube portion when in the filter coupling configuration, such that the filter is configured to be coupled to the collet when the collet is in the filter coupling configuration and the filter is configured to be decoupled from the collet when the collet is in the filter decoupling configuration.

The filter may be in a radially constrained configuration when disposed within the delivery sheath.

The delivery sheath may be configured to retract to deploy the filter from the delivery sheath.

The filter coupling mechanism may be further configured to engage the filter, from a decoupled configuration, at either the first axial portion or the second axial portion of the filter.

The delivery sheath may be configured to extend to dispose the engaged filter within the delivery sheath.

The filter deployment assembly may further comprise one or more radiopaque markers.

The radiopaque markers may comprise gold.

III. Methods of Deploying Filters

In one embodiment, a method of deploying a filter may comprise: (1) coupling a filter to a filter deployment device by disposing a tube portion of the filter around a filter coupling mechanism; (2) actuating a deployment actuator to extend a delivery sheath over the coupled filter; (3) introducing the sheathed filter into a body lumen; (4) actuating the deployment actuator to retract the delivery sheath to deploy the filter; and (5) decoupling the filter from the filter deployment device by actuating a coupling mechanism.

The step of decoupling may comprise distally displacing an inner member of the filter coupling mechanism in relation to a collet at a distal end of an outer member of the filter coupling mechanism by actuating the coupling mechanism such that the collet disengages from the filter.

The filter may comprise a first tube portion and second tube portion.

Coupling the filter may comprise engaging an annular taper of the inner member with the collet such that a diameter of the collet increases and the collet engages one of the first and second tube portions.

Decoupling the filter may comprise disengaging an annular taper of the inner member from the collet such that a diameter of the collet decreases and the collet disengages one of the first and second tube portions.

IV. Further Methods of Deploying Filters

In one embodiment, a method of deploying a filter may comprise: (1) coupling a filter to a filter deployment device; (2) introducing the filter into a body lumen; (3) deploying the filter; and (4) decoupling the filter from the filter deployment device, such that decoupling the filter is independent of deploying the filter.

The method may further comprise at least distally or proximally displacing the deployed filter within the body lumen.

The method may further comprise recoupling the decoupled filter to the filter deployment device.

The method may further comprise removing the recoupled filter from the body lumen.

The method may further comprise: (1) repositioning the recoupled filter within the body lumen; and (2) decoupling the repositioned filter from the filter deployment device.

V. Additional Filter Deployment Devices

In one embodiment, a filter deployment device may be configured to limit inadvertent decoupling of a filter, the filter deployment device may comprise: (1) a delivery sheath; (2) a deployment member axially displaceable within the delivery sheath; (3) a filter coupling mechanism disposed adjacent a distal end of the deployment member, the filter coupling mechanism configured to releasably couple a filter to the deployment member independent of the delivery sheath; (4) a coupling actuator coupled to the filter coupling mechanism, wherein actuation of the coupling actuator is configured to decouple a filter with respect to the delivery sheath; and (5) a release safety that permits decoupling of the filter only when the filter is in a deployed configuration.

The filter deployment device may further comprise a deployment actuator operatively coupled to the delivery sheath, wherein the deployment actuator is displaceable between a first position and a second position such that displacement of the deployment actuator from the first position to the second position is configured to deploy a filter.

The deployment actuator may proximally displace the delivery sheath with respect to a filter.

The filter coupling mechanism may comprise: (1) an outer member operatively coupled to both the deployment actuator and the coupling actuator, the outer member configured to releasably couple a filter; and (2) an inner member axially displaceable within the outer member and operatively coupled to the coupling actuator, wherein actuation of the coupling actuator simultaneously displaces both the outer member and the inner member with respect to the delivery sheath when the deployment actuator is disposed in the first position, and wherein actuation of the coupling actuator displaces the inner member with respect to the outer member when the deployment actuator is disposed in the second position.

The outer member may comprise a collet adjacent a distal end of the outer member, the collet configured to releasably couple the filter to the outer member.

The collet may comprise a plurality of flexible legs and the inner member may comprise an enlarged distal section configured to engage the collet and radially outward bias the legs of the collet to couple a filter to the outer member, and wherein disengagement of the enlarged distal section is configured to permit radial inward displacement of the legs of the collet to decouple the filter from the outer member.

The filter deployment device may further comprise: (1) a first biasing member operatively disposed between the coupling actuator and a biasing member perch; and (2) a second biasing member operatively disposed between the biasing member perch and a biasing member perch stop, wherein the biasing member perch is displaceable with respect to the biasing member perch stop when the deployment actuator is in the first position and the biasing member perch is fixed with respect to the biasing member perch stop when the deployment actuator is in the second position.

The first biasing member may exert a greater biasing force than the second biasing member.

A first biasing force exerted by the first biasing member may displace the biasing member perch when the coupling actuator is displaced and the deployment actuator is in the first position, and wherein a second biasing force exerted by the second biasing member may resist displacement of the biasing member perch when the coupling actuator is displaced and the deployment actuator is in the first position.

The first biasing member may comprise a first spring and the second biasing member may comprise a second spring.

The filter deployment device may further comprise one or more radiopaque markers.

The radiopaque markers may comprise gold.

VI. Methods of Avoiding Inadvertent Decoupling of a Filter

In one embodiment, a method of avoiding inadvertent decoupling of a filter from a filter deployment device may comprise: (1) coupling a filter to a filter coupling mechanism; (2) actuating a deployment actuator to extend a delivery sheath over the filter; (3) introducing the sheathed filter into a body lumen; (4) actuating the deployment actuator to retract the sheath to deploy the filter; and (5) decoupling the filter from the filter deployment device by actuating a coupling mechanism, wherein actuation of the coupling mechanism is configured to decouple the filter only when the filter is deployed from the delivery sheath.

VII. Additional Filter Deployment Devices

A filter deployment device may be configured to limit inadvertent decoupling of a filter, the filter deployment device may comprise: (1) an introducer sheath; (2) a deployment member axially displaceable within the introducer sheath; (3) a filter coupling mechanism disposed adjacent a distal end of the deployment member, the filter coupling mechanism configured to releasably couple a filter to the deployment member independent of the introducer sheath; (4) a coupling actuator coupled to the filter coupling mechanism, wherein actuation of the coupling actuator is configured to decouple a filter with respect to the introducer sheath; and (5) a release safety that permits decoupling of the filter only when the filter is in a deployed configuration.

The filter deployment device may further comprise a hub operatively coupled to the introducer sheath, wherein the hub is displaceable between a disengaged position and an engaged position such that displacement of the hub from the disengaged position to the engaged position is configured to deploy a filter.

The hub may proximally displace the introducer sheath with respect to a filter.

The filter coupling mechanism may comprise: (1) an outer member operatively coupled to both a first biasing member and the coupling actuator, the outer member configured to releasably couple a filter; and (2) an inner member axially displaceable within the outer member and operatively coupled to the coupling actuator, wherein actuation of the coupling actuator simultaneously displaces both the outer member and the inner member with respect to the introducer sheath when the hub is disposed in the unengaged position, and wherein actuation of the coupling actuator displaces the inner member with respect to the outer member when the hub is disposed in the engaged position.

The outer member may comprise a collet adjacent a distal end of the outer member, the collet may be configured to releasably couple the filter to the outer member.

The collet may comprise a plurality of flexible legs and the inner member comprises an enlarged distal section configured to engage the collet and radially outward bias the legs of the collet to couple a filter to the outer member, and wherein disengagement of the enlarged distal section is configured to permit radial inward displacement of the legs of the collet to decouple the filter from the outer member.

The filter deployment may further comprise: (1) a first biasing member operatively disposed between the coupling actuator and a biasing member perch; and (2) a perch engagement tube operatively disposed between the biasing member perch and a filter packaging cartridge, wherein the biasing member perch is displaceable with respect to a biasing member perch stop when the hub is in the unengaged position and the biasing member perch is fixed with respect to the biasing member perch stop when the hub is in the engaged position.

The first biasing member may comprise a first spring.

The filter deployment device may further comprise one or more radiopaque markers.

The radiopaque markers may comprise gold.

VIII. Methods of Avoiding Inadvertent Decoupling of a Filter

In one embodiment, a method of avoiding inadvertent decoupling of a filter from a filter deployment device may comprise: (1) introducing a sheathed filter into a body lumen; (2) displacing an introducer sheath to deploy the filter; and (3) decoupling the filter from the filter deployment device by actuating a coupling mechanism, wherein actuation of the coupling mechanism is configured to decouple the filter only when the filter is deployed from the introducer sheath.

IX. Filter Packing Cartridges

In one embodiment, a filter packaging cartridge may comprise: (1) an elongate member configured to at least partially retain a filter; and (2) a toggling member operatively coupled to the elongate member, the toggling member configured to toggle the elongate member between a first configuration and a second configuration, wherein the first configuration exposes a first end of a filter, wherein the second configuration exposes a second end of the filter, and wherein only the exposed end of the filter is available for coupling to a filter deployment device.

The cartridge may comprise indicia configured to indicate to a user how to selectively orient a filter for coupling to a filter deployment device.

A first indicia may indicate to a user how to selectively couple a filter to a filter deployment device for jugular insertion of the filter.

The first indicia may only be visible when the first end of the filter is exposed.

A second indicia may indicate to a user how to selectively couple a filter to a filter deployment device for femoral insertion of the filter.

The second indicia may only be visible when the second end of the filter is exposed.

The toggling member may comprise a tab configured to orient a filter with respect to a filter deployment device to control which end of the filter is positioned downstream when deployed in a body lumen.

X. Filter Packing Cartridge Kits

In one embodiment, a filter packaging cartridge kit may comprise: (1) a filter; (2) an elongate member configured to retain the filter; and (3) a toggling member operatively coupled to the elongate member, the toggling member configured to toggle the elongate member between a first configuration and a second configuration, wherein the first configuration exposes a first end of a filter, wherein the second configuration exposes a second end of the filter, and wherein only the exposed end of the filter is available for coupling to a filter deployment device.

At least one of the cartridge and the filter may comprise indicia of the orientation of the filter within the elongate member.

The cartridge may comprise indicia configured to indicate to a user how to selectively orient the filter for coupling to a filter deployment device.

A first indicia may indicate to a user how to selectively couple the filter to the filter deployment device for jugular insertion of the filter.

The first indicia may only be visible when the first end of the filter is exposed.

A second indicia may indicate to a user how to selectively couple the filter to the filter deployment device for femoral insertion of the filter.

The second indicia may only be visible when the second end of the filter is exposed.

The toggling member may comprise a tab configured to orient the filter with respect to the filter deployment device to control which end of the filter is positioned downstream when deployed in a body lumen.

XI. Methods of Coupling Vascular Filters to Deployment Devices

In one embodiment, a method of coupling a vascular filter to a deployment device comprises: (1) obtaining a vascular filter disposed within a filter packaging cartridge; (2) toggling the cartridge relative to the filter such that one of a first or second end of the filter is available for coupling to a filter deployment device; and (3) coupling the available end of the filter to the filter deployment device.

Toggling the cartridge may further comprise displacing the cartridge between at least a first position and a second position such that one of the first end or the second end of the filter is exposed.

Coupling the filter may further comprise using indicia on the cartridge to selectively orient the filter for coupling to a filter deployment device.

Coupling the filter may further comprise using indicia on the filter to selectively orient the filter for coupling to a filter deployment device.

Coupling the filter may further comprise selectively coupling the filter to the filter deployment device for jugular insertion of the filter.

Coupling the filter may further comprise selectively coupling the filter to the filter deployment device for femoral insertion of the filter.

Coupling the filter may further comprise selectively coupling the filter to the filter deployment device for downstream disposition of the filter in a body lumen.

XII. Filters

In one embodiment, a filter for a body lumen may comprise: (1) a body member; and (2) a plurality of extensions coupled to and projecting from the body member, at least one of the extensions may comprise: (1) an outside surface; and (2) an inside surface, wherein the inside surface tapers to a point.

A cross section of the at least one extension may be substantially trilateral.

At least a portion of the outside surface of the at least one extension may be configured to contact a surface of a body lumen.

The inside surface may be configured to slice through tissue ingrowth or tissue encapsulation in a body lumen.

The inside surface may be configured to facilitate retrieval of the filter from a body lumen through ingrown tissue or tissue which has encapsulated a portion of a geometry of the filter.

Each extension may comprise: (1) a first peak; (2) a second peak disposed longitudinally from the first peak; (3) a valley, the valley extending longitudinally between the first and second peaks; and (4) a leg, wherein the leg is disposed between the first peak and the body member.

The legs may extend radially outward from the body member when the filter is deployed.

A plurality of barbs may be formed from center portions of the extensions.

Each barb may be configured to align with a portion of the extension to which the barb is coupled, when the extensions are drawn into a filter sheath.

The filter may be integrally formed.

XIII. Methods of Retrieving Filters

In one embodiment, a method of retrieving a body lumen filter from a body lumen may comprise: (1) coupling a filter comprising a plurality of extensions to a filter retrieval device; (2) displacing the filter proximally such that an inside surface of the extensions each comprising a taper to a point that slices through ingrown tissue; and (3) removing the coupled filter from a body lumen.

The examples and embodiments disclosed herein are to be construed as merely illustrative and exemplary, and not a limitation of the scope of the present disclosure in any way. It will be apparent to those having skill in the art with the aid of the present disclosure that changes may be made to the details of the above-described embodiments without departing from the underlying principles of the disclosure herein. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. It is intended that the scope of the invention be defined by the claims appended hereto and their equivalents.

The invention claimed is:

1. A filter deployment assembly, comprising:
 a delivery sheath;
 a filter coupling mechanism;
 the filter coupling mechanism comprising an actuating member and an outer member, wherein the filter coupling mechanism is axially displaceable within the delivery sheath; the filter deployment assembly further comprising,
 a coupling actuator coupled to the filter coupling mechanism, wherein actuation of the coupling actuator is configured to decouple a filter with respect to the filter deployment assembly;
 a first biasing member operatively disposed between the coupling actuator and a biasing member perch; and
 a second biasing member operatively disposed between the biasing member perch and a biasing member perch stop;
 wherein the filter coupling mechanism is configured to attach to the filter independent of the delivery sheath, the filter coupling mechanism configured to engage the filter through radial expansion of the outer member due to relative proximal displacement of the actuating member with respect to the outer member, the filter coupling mechanism actuatable to release the filter, the actuating member actuatable from a proximal end of the filter deployment assembly,
 wherein the actuating member comprises a tapered section,
 wherein the filter coupling mechanism is configured to disengage the filter through radial retraction of the outer member due to relative distal displacement of the tapered section with respect to the outer member, and
 wherein the biasing member perch is displaceable with respect to the biasing member perch stop when the coupling actuator is in a first position and the biasing member perch is fixed with respect to the biasing member perch stop when the deployment actuator is in a second position.

2. The filter deployment assembly of claim 1, wherein the filter coupling mechanism is configured to proximally and distally displace the filter independent of the position of the filter with respect to the delivery sheath.

3. The filter deployment assembly of claim 1, wherein the filter coupling mechanism is configured to proximally and distally displace the filter when the filter is disposed outside the delivery sheath.

4. The filter deployment assembly of claim 1, wherein the actuating member is axially displaceable with respect to the outer member.

5. The filter deployment assembly of claim 4, wherein the actuating member comprises an inner member axially displaceable within the outer member.

6. The filter deployment assembly of claim 5, wherein the outer member comprises a collet adjacent a distal end of the outer member, the collet configured to releasably couple the filter to the outer member.

7. The filter deployment assembly of claim 6, wherein the inner member comprises:
  a proximal section;
  a middle section; and
  a distal section configured to engage the collet, wherein an outside diameter of the distal section is greater than an outside diameter of the middle section.

8. The filter deployment assembly of claim 7, wherein the tapered section comprises an annular taper disposed between the distal section and the middle section, the annular taper configured to engage an inside surface of the collet such that a portion of the collet is biased radially outward when the collet is in a filter coupling configuration.

9. The filter deployment assembly of claim 8, wherein the annular taper is further configured to disengage from the inside surface of the collet when the collet is in a filter decoupling configuration.

10. The filter deployment assembly of claim 1, wherein the delivery sheath is configured to retract to deploy the filter when the filter is disposed within the delivery sheath.

11. The filter deployment assembly of claim 1, wherein the filter coupling mechanism is further configured to recouple a decoupled filter.

12. The filter deployment assembly of claim 1, further comprising the filter axially displaceable within the delivery sheath, the filter comprising:
  a first axial portion adjacent a first end of the filter; and
  a second axial portion adjacent a second end of the filter, wherein the filter coupling mechanism is configured to releasably couple to either one of the first axial portion or the second axial portion of the filter.

13. The filter deployment assembly of claim 12, wherein the first axial portion of the filter comprises a first tube portion and the second axial portion of the filter comprises a second tube portion and wherein a collet of the filter coupling mechanism is configured to be at least partially disposed within at least one of the first and second tube portions.

14. The filter deployment assembly of claim 13, wherein at least one of an inside diameter of the first tube portion of the first axial portion and an inside diameter of the second tube portion of the second axial portion is greater than an outside diameter of a portion of the collet disposed within the first or second tube portion when in a filter decoupling configuration,
  and wherein an outside diameter of the portion of the collet disposed within the tube portion when the filter deployment assembly is in a filter coupling configuration is biased into contact with at least one of the inside diameter of the first tube portion of the first axial portion and the inside diameter of the second tube portion of the second axial portion, such that the filter is configured to be coupled to the collet when the collet is in the filter coupling configuration and the filter is configured to be decoupled from the collet when the collet is in the filter decoupling configuration.

15. The filter deployment assembly of claim 12, further comprising a filter packing cartridge, the cartridge comprising:
  an elongate member configured to retain the filter; and
  a toggling member operatively coupled to the elongate member, the toggling member configured to toggle the elongate member between a first configuration and a second configuration, wherein the first configuration exposes the first end of the filter, wherein the second configuration exposes the second end of the filter, and wherein only the exposed end of the filter is available for coupling to a filter coupling mechanism.

16. The filter deployment assembly of claim 15, wherein at least one of the cartridge and the filter comprises indicia of the orientation of the filter within the elongate member.

17. The filter deployment assembly of claim 1, further comprising:
  a release safety that permits decoupling of the filter only when the filter is in a deployed configuration.

18. The filter deployment assembly of claim 1, wherein the first biasing member exerts a greater biasing force than the second biasing member.

19. The filter deployment assembly of claim 1, further comprising an introducer sheath, wherein the delivery sheath is axially displaceable within the introducer sheath.

* * * * *